US012806401B2

(12) United States Patent
Alwatban et al.

(10) Patent No.: US 12,806,401 B2
(45) Date of Patent: Nov. 24, 2026

(54) SYSTEMS AND METHODS FOR DETECTING SUCTION EVENTS IN BLOOD PUMPS

(71) Applicant: ABIOMED, Inc., Danvers, MA (US)

(72) Inventors: Mohammed Alwatban, Danvers, MA (US); Maxim Daschewski, Aachen (DE); Qing Tan, Danvers, MA (US); Andre Chuev, Aachen (DE); Ahmad El Katerji, Danvers, MA (US)

(73) Assignee: ABIOMED, Inc., Danvers, MA (US)

( * ) Notice: Subject to any disclaimer, the term of this patent is extended or adjusted under 35 U.S.C. 154(b) by 626 days.

(21) Appl. No.: 17/971,269

(22) Filed: Oct. 21, 2022

(65) Prior Publication Data

US 2023/0131738 A1 Apr. 27, 2023

Related U.S. Application Data

(60) Provisional application No. 63/270,940, filed on Oct. 22, 2021.

(51) Int. Cl.
*A61N 1/362* (2006.01)
*A61M 1/10* (2006.01)
(Continued)

(52) U.S. Cl.
CPC ........ *A61M 60/148* (2021.01); *A61M 60/178* (2021.01); *A61M 60/422* (2021.01)

(58) Field of Classification Search
CPC .............. A61M 60/148; A61M 60/178; A61M 60/216; A61M 60/422; A61M 60/546;
(Continued)

(56) References Cited

U.S. PATENT DOCUMENTS 6,572,530 B1 6/2003 Araki et al.
6,991,595 B2 1/2006 Burke et al.
(Continued)

FOREIGN PATENT DOCUMENTS

CN 102740902 A 10/2012
CN 110115786 A 8/2019
(Continued)

OTHER PUBLICATIONS

International Search Report and Written Opinion for International Application No. PCT/US2022/047426 dated Feb. 10, 2023 (13 pages).

(Continued)

*Primary Examiner* — Jon Eric C Morales
(74) *Attorney, Agent, or Firm* — BOTOS CHURCHILL IP LAW LLP

(57) ABSTRACT

Systems and methods for detecting suction events in blood pumps by monitoring pump motor current. A pump suction event is detected based on a comparison of a pulsatility index that is calculated based on a filtered pump motor current signal with a first predetermined threshold or based on a comparison of a calculated index associated with a normalized band-pass filtered pump motor current signal with a second predetermined threshold. A suction event is also detected based on comparisons of both the calculated pulsatility index and the calculated index associated with the normalized band-pass filtered pump motor current signal with respective first and second predetermined thresholds.

26 Claims, 16 Drawing Sheets

(51) Int. Cl.

| | |
|---|---|
| ***A61M 1/12*** | (2006.01) |
| ***A61M 60/148*** | (2021.01) |
| ***A61M 60/178*** | (2021.01) |
| *A61M 60/422* | (2021.01) |

(58) Field of Classification Search
CPC ........ A61M 2205/3334; A61M 60/523; A61M 60/538; A61M 2205/18; A61M 2205/3317; A61M 2205/3331; A61M 2205/3365; A61M 2205/50; A61M 2205/52; A61M 2205/8206; A61M 60/196; A61M 60/20; A61M 60/205; A61M 60/237; A61M 60/50; A61M 60/531; A61M 60/562; A61M 60/592
See application file for complete search history.

(56) References Cited

U.S. PATENT DOCUMENTS

| | | | | |
|---|---|---|---|---|
| 2004/0215050 | A1 | 10/2004 | Morello | |
| 2005/0004418 | A1* | 1/2005 | Morello .............. | A61M 60/178 600/16 |
| 2013/0006130 | A1 | 1/2013 | Olde et al. | |
| 2016/0058930 | A1 | 3/2016 | Medvedev et al. | |
| 2017/0209632 | A1* | 7/2017 | Pierce ................. | A61M 60/178 |
| 2018/0353667 | A1 | 12/2018 | Moyer et al. | |
| 2019/0307938 | A1 | 10/2019 | Reyes et al. | |

FOREIGN PATENT DOCUMENTS

| | | | |
|---|---|---|---|
| CN | 111479500 | A | 7/2020 |
| CN | 111989127 | A | 11/2020 |
| EP | 1354606 | A1 | 10/2003 |
| JP | 2004501678 | A | 1/2004 |
| JP | 2000504977 | A | 4/2005 |
| JP | 2005514094 | A | 5/2005 |
| WO | 9819624 | A2 | 5/1998 |
| WO | 0172352 | A2 | 10/2001 |
| WO | 03057013 | A2 | 7/2003 |
| WO | 2022261580 | A1 | 12/2022 |

OTHER PUBLICATIONS

Office Action issued in Taiwanese Patent Application No. 111140191, dated Dec. 15, 2025 (16 pp.).

Gwak, et al. In Vitro Evaluation of Multiobjective Hemodynamic Control of a Heart-Assist Pump. ASAIO Journal 51(4): p. 329-335, Jul. 2005. I DOI:10.1097/01.mat.0000169122.64794.28.

Office Action issued in Indian Patent Application No. 202417037471 on May 8, 2026 (8 pp.).

Office action issued in Japanese Patent Application No. 2024-519986, dated Aug. 25, 2026 (16 pp.).

Office Action from corresponding Chinese Patent Application No. 202280080158.7 dated Sep. 12, 2026 (18 pp.).

* cited by examiner

SYSTEMS AND METHODS FOR DETECTING SUCTION EVENTS IN BLOOD PUMPS

CROSS REFERENCE TO RELATED APPLICATION

This application claims priority to and the benefit of U.S. Provisional Application No. 63/270,940 filed Oct. 22, 2021, the entirety of which is incorporated by reference herein.

TECHNICAL FIELD

The present technology relates to systems and methods for detecting suction events in blood pumps, such as heart pumps, using the pump motor current.

BACKGROUND

Fluid pumps, such as blood pumps, are used in the medical field in a wide range of applications and purposes. An intravascular blood pump is a pump that can be advanced through a patient's vasculature, i.e., veins and/or arteries, to a position in the patient's heart or elsewhere within the patient's circulatory system. For example, an intravascular blood pump may be inserted via a catheter and positioned to span a heart valve. The intravascular blood pump is typically disposed at the end of the catheter. Once in position, the pump may be used to assist the heart and pump blood through the circulatory system and, therefore, temporarily reduce workload on the patient's heart, such as to enable the heart to recover after a heart attack. An exemplary intravascular blood pump is available from Abiomed, Inc., Danvers, MA under the tradename Impella® heart pump.

Such pumps can be positioned, for example, in a cardiac chamber, such as the left ventricle, to assist the heart. In this case, the blood pump may be inserted via a femoral artery by means of a hollow catheter and introduced up to and into the left ventricle of a patient's heart. From this position, the blood pump inlet sucks in blood and the blood pump outlet expels the blood into the aorta. In this manner, the heart's function may be replaced or at least assisted by operation of the pump.

Each intravascular blood pump is typically connected to a respective external heart pump controller that controls the heart pump, such as motor speed, and collects and displays operational data about the blood pump, such as heart signal level, battery temperature, blood flow rate and plumbing integrity. An exemplary heart pump controller is available from Abiomed, Inc. under the trade name Automated Impella Controller®. The controller raises alarms when operational data values fall beyond predetermined values or ranges, for example if a leak or loss of suction is detected. The controller includes a video display screen as a human user interface, on which the operational data and/or alarms are displayed.

As the blood pump draws blood into the pump using suction, there is a potential that, should the pump suction inlet be too close or adjacent to the cardiac tissue, a suction event might occur. A suction event may occur when the pump inlet interacts with cardiac tissues, causing partial or complete blockage of pump flow. Sustained suction events could damage the patient's heart, compromise pump function, and cause inadequate perfusion. Additionally, suction events could also lead to hemolysis. Therefore, a need exists to detect suction so that suction events can be resolved.

BRIEF SUMMARY

Described herein are systems and methods for detecting suction events in blood pumps.

In one aspect, a blood pump is provided comprising: an inlet, an outlet, a rotor, a motor for driving rotation of the rotor to convey blood from the inlet to the outlet, and at least one processor. The at least one processor is configured to: monitor a motor current signal of the motor, filter the motor current signal, calculate a pulsatility index of the motor current signal based on the filtered motor current signal, compare the calculated pulsatility index to a predetermined threshold, and detect an occurrence of a suction event based on the comparison.

In another aspect, a blood pump is provided comprising: an inlet, an outlet, a rotor, a motor for driving rotation of the rotor to convey blood from the inlet to the outlet, and at least one processor. The at least one processor is configured to: monitor a motor current signal of the motor, low-pass filter the motor current signal, band-pass filter the low-pass filtered motor current signal, normalize the band-pass filtered motor current signal, calculate an index value based on the normalized band-pass filtered motor current signal, compare the calculated index value to a predetermined threshold, and detect an occurrence of a suction event based on the comparison.

In another aspect, a blood pump is provided comprising: an inlet, an outlet, a rotor, a motor for driving rotation of the rotor to convey blood from the inlet to the outlet, and at least one processor configured to: monitor a motor current signal of the motor, low-pass filter the motor current signal, calculate a pulsatility index of the motor current signal based on the low-pass filtered motor current signal, band-pass filter the low-pass filtered motor current signal, normalize the band-pass filtered motor current signal, calculate an index value based on the normalized band-pass filtered signal, compare the calculated pulsatility index to a first predetermined threshold and the calculated index value to a second predetermined threshold, and detect an occurrence of a suction event based on the comparison of the calculated pulsatility index to the first predetermined threshold and the calculated index value to the second predetermined threshold.

DETAILED DESCRIPTION

Figure 1A:
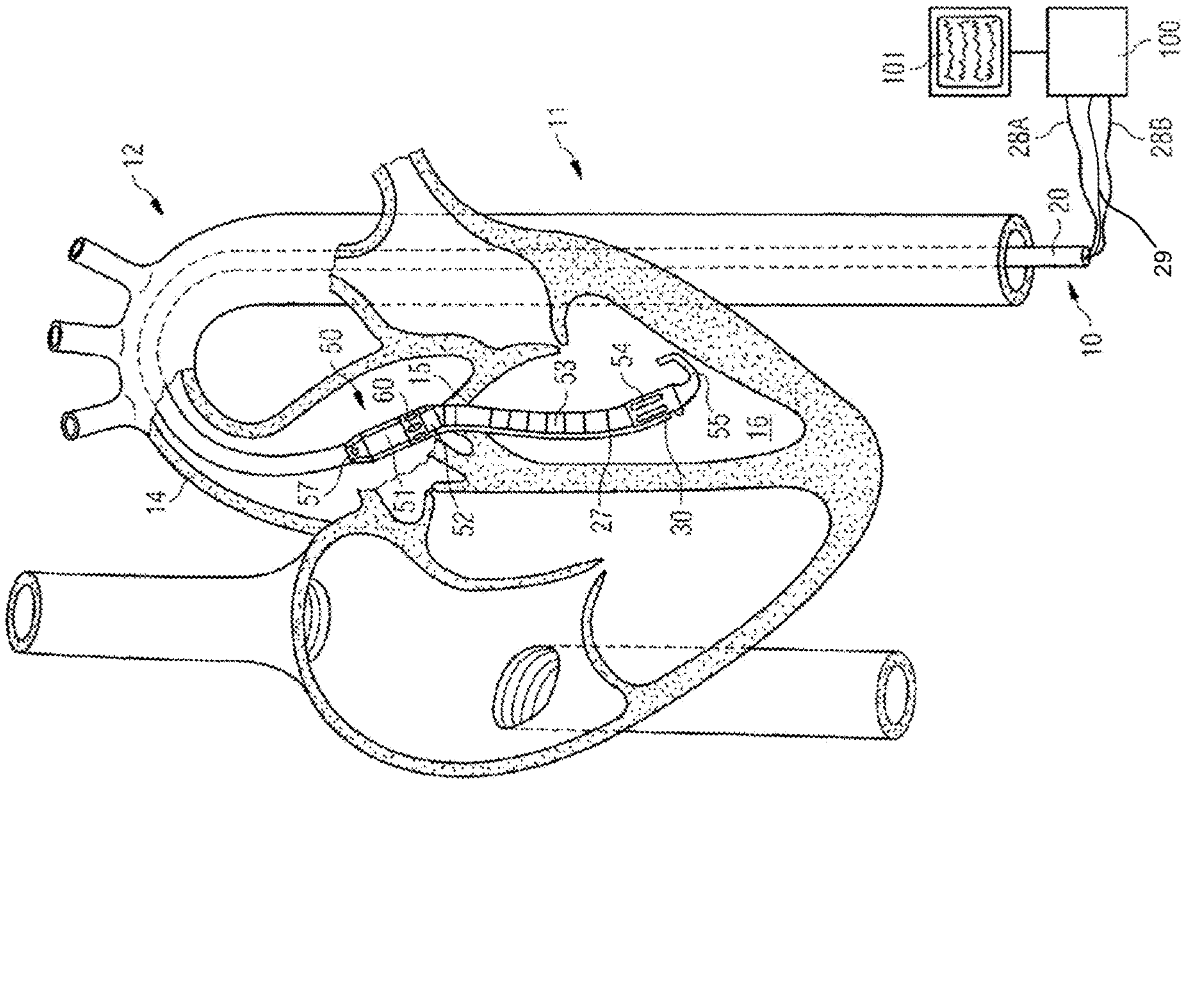
FIG. 1A (PRIOR ART)
FIG. 1A illustrates a prior art pump inserted into a heart.

Aspects of the present disclosure are described in detail with reference to the drawing figures wherein like reference numerals identify similar or identical elements. It is to be understood that the disclosed aspects are merely examples of the disclosure, which may be embodied in various forms. Well-known functions or constructions are not described in detail to avoid obscuring the present disclosure in unnecessary detail. Therefore, specific structural and functional details disclosed herein are not to be interpreted as limiting, but merely as a basis for the claims and as a representative basis for teaching one skilled in the art to variously employ the present disclosure in virtually any appropriately detailed structure.

Traditionally, in blood pumps, such as catheter-based heart pumps inserted into a ventricle of the patient, suction events, which may be caused by an interaction between the inlet of the pump and cardiac tissue, are detected using both pressure sensors and motor current.

Figure 1B:
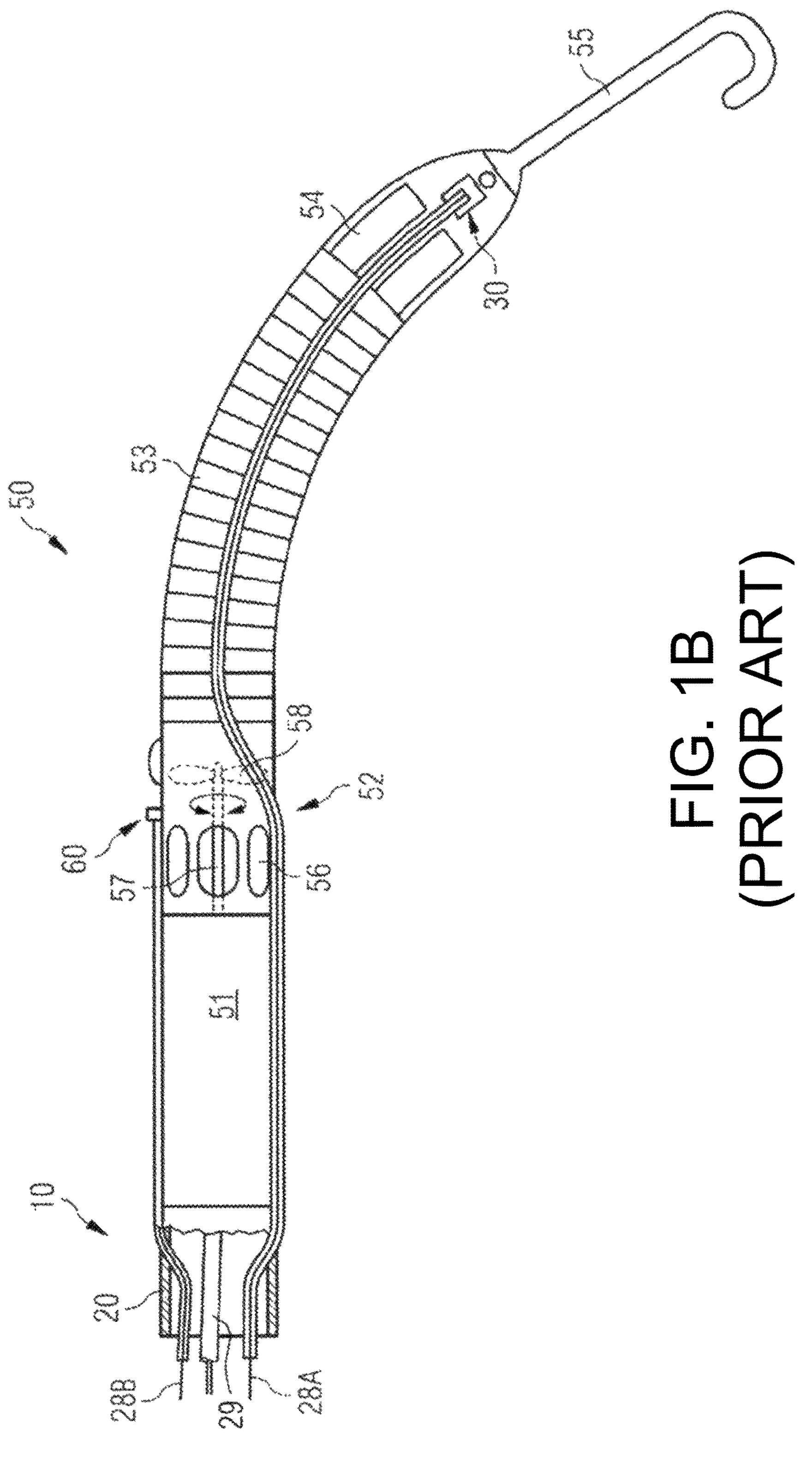
FIG. 1B (PRIOR ART)
FIG. 1B illustrates a portion of the prior art pump of FIG. 1A.

For example, a prior art catheter-based heart pump is shown in FIGS. 1A and 1B. The blood pump of FIGS. 1A and 1B is based on a catheter 10 (catheter-based blood pump), by means of which the blood pump is temporarily introduced through the aorta 12 and the aortic valve 15 into the left ventricle 16 of a heart. As shown in more detail in FIG. 1B, the blood pump comprises in addition to the catheter 10 a rotary pumping device 50 fastened to the end of a catheter tube 20. The rotary pumping device 50 comprises a motor section 51 and a pump section 52 located at an axial distance therefrom. A flow cannula 53 is connected to the pump section 52 at its one end, extends from the pump section 52 and has an inflow cage 54 located at its other end. The inflow cage 54 has attached thereto an atraumatic tip 55. The pump section 52 comprises a pump housing with outlet openings 56. Further, the pumping device 50 comprises a drive shaft 57 protruding from the motor section 51 into the pump housing of the pump section 52. The drive shaft 57 drives an impeller 58 as a thrust element by means of which, during operation of the blood pump, blood can be sucked through the inflow cage 54 (which forms an inlet) and discharged through the outlet openings 56 (which form an outlet) on the other side of the aortic valve 15.

In FIGS. 1A and 1B, three lines, two signal lines 28A and 28B and a power-supply line 29 for supplying an electrical current to the motor section 51, pass through the catheter tube 20 of the catheter 10 to the pumping device 50. The two signal lines 28A, 28B and the power-supply line 29 are attached at their proximal end to a control device 100.

As shown in FIG. 1B, the signal lines 28A, 28B are coupled blood pressure sensors with corresponding sensor heads 30 and 60, respectively, which are located externally on the housing of the pump section 52. The sensor head 60 of the first pressure sensor is associated with signal line 28B. The signal line 28A is associated with and connected to the sensor head 30 of the second blood pressure sensor. Signals of the pressure sensors, which carry the respective information on the pressure at the location of the sensor and which may be of any suitable physical origin, e.g., of optical, hydraulic or electrical, etc., origin, are transmitted via the respective signal lines 28A, 28B to corresponding inputs of control device 100.

As described above, the blood pressure sensed by sensors 30, 60 and the motor current supplied via power supply line 29 to motor section 51, traditionally, may be used by control device 100 to determine if a suction event is occurring. However, some pumps may not include pressure sensors, and may locate the pump motor outside the patient to decrease the maximum outer diameter of the pump when the pump is inserted and removed from the patient.

Figure 2A:
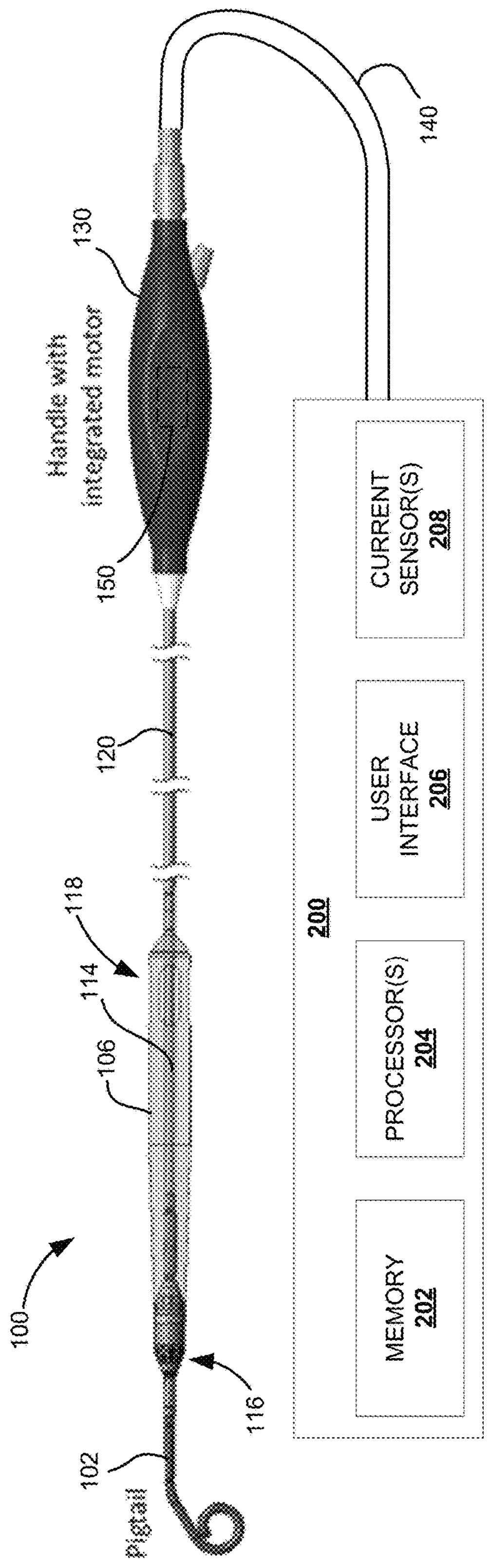
FIG. 2A illustrates a pump system in accordance with the present technology.
Figure 2B:
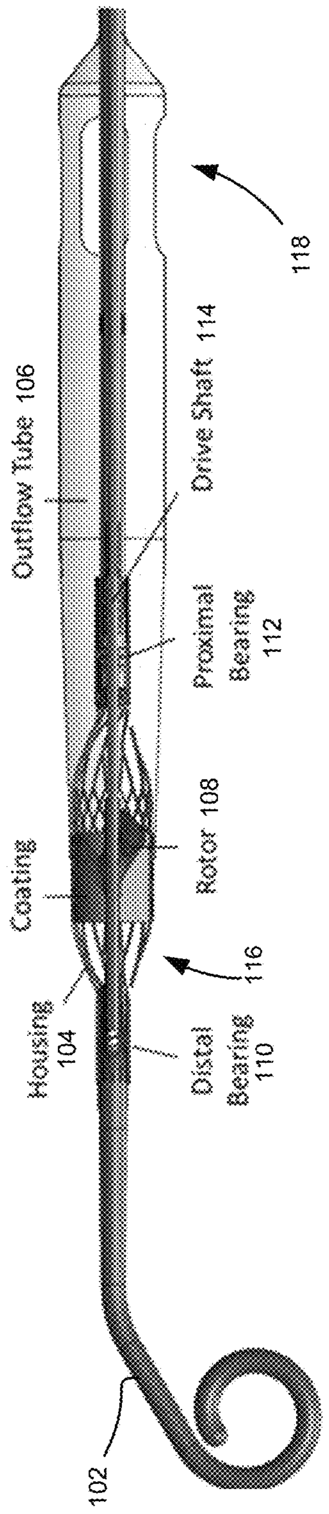
FIG. 2B is a cross-sectional view of a portion of the pump system of FIG. 2A in accordance with the present technology.

For example, a pump system 100 is shown in FIGS. 2A and 2B coupled to a control unit 200 in accordance with the present technology. Pump 100 includes a distal atraumatic tip 102, a coated pump housing 104 surrounding a rotor 108, an outflow tube 106, distal bearing 110, proximal bearing 112, inlet 116, outlet 118, catheter 120, handle 130, cable 140, and motor 150. In one aspect, pump housing 104 is a frame structure that is formed by a mesh with openings which may, at least in part, be covered by an elastic material. A proximal portion of pump housing 104 extends into and is mounted in the hollow interior of outflow tube 106 and a distal portion of pump housing 104 extends distally beyond the distal end of outflow tube 106. The exposed openings in the mesh pump housing 104 extending distally beyond outflow tube 106 form the inlet 116 of pump 100. The proximal end of outflow tube 106 includes a plurality of openings that form the outlet 118 of pump 100. Rotor 108 is rotationally mounted between bearing 110, 112 and is coupled to a distal end of flexible drive shaft 114. Drive shaft 114 extends through catheter 120, through the hollow interior of outflow tube 106, into handle 130 and is coupled to motor 130, which is integrated in handle 130. The proximal end of handle 130 is coupled via cable 140 to control unit 200.

Control unit 200 includes one or more memory 202, one or more processors 204, user interface 206, and one or more current sensors 208. Processor(s) 204 may comprise one or more microcontrollers, one or more microprocessors, one or more application specific integrated circuits (ASICs), one or more digital signal processors, program memory, or other similar components. Processor 204 is communicatively coupled to and configured to control the other components (e.g., 202, 206, 208) of control unit 200 and the operation of pump 100. In one aspect, control device 200 is an Automated Impella Controller® from Abiomed, Inc., Danvers, MA. In some aspects, memory 202 is included in processor 204 internally.

During operation, processor 204 controls the electrical power delivered to motor 150 (e.g., by controlling a power supply (not shown)) by a power supply line (not shown) in cable 140. By controlling the power delivered to motor 150, processor 204 can control the speed of the motor 150. In one aspect, processor 204 may monitor the motor current using one or more current sensors 208 that measure and sample the motor current. Current sensor 208 may be included in control unit 200 or along any portion of the power supply line in cable 140. In another aspect, current sensor 208 may be included in motor 130 and processor 204 may monitor and measure the motor current via a data line (not shown) in cable 140 coupled to processor 204 and motor 150.

Memory 202 may store computer-readable instructions and other information for various functions of the components of control unit 200. In one aspect, memory 202 includes volatile and/or non-volatile memory, such as, an electrically erasable programmable read-only memory (EEPROM).

User interface 206 may include means for receiving user input, such as, buttons, switches, knobs, etc. Moreover, user interface 206 may include a display for displaying information and one or more indicators, such as light indicators, audio indicators, etc., for conveying information and/or providing alerts regarding the operation of pump 100.

Pump 100 is insertable into the patient's body, e.g., into a left ventricle of the heart, with an introducer system. In one aspect, housing 104, rotor 108, and outflow tube 106 are radially compressible to enable pump 100 to achieve a relatively small outer diameter of, for example, 9 Fr (3 mm) during insertion. When pump 100 is inserted into the patient, e.g., into a left ventricle in a similar manner described above with reference to the pump of FIGS. 1A and 1B, handle 130 and motor 150 are disposed outside the patient. Motor 150 is controlled by processor 204 to drive rotation of drive shaft 114 and rotor 108 to convey blood from inlet 116 to outlet 118. It is to be appreciated that rotor 108 may be rotated by motor 150 in reverse to convey blood in the opposite direction (in this case, the openings of 118 form the inlet and the openings of 116 form the outlet). In one aspect, pump 100 is intended to be used during high-risk procedures for a duration of up to six hours, though it should be understood that the presently disclosed technology is not limited to any particular types of procedures and/or use durations.

Since, the pump 100 lacks the pressure sensors included in traditional pumps, such as shown in FIGS. 1A and 1B, prior suction detection methods or algorithms relying on pressure signals cannot be used with pump 100. However, when pump 100 is inserted into a patient, suction events can still occur and need to be detected to be resolved in a timely manner such that the risk of damage to the patient and/or to the pump 100 may be reduced. Thus, there is a need to enable suction detection in pumps that do not include pressure sensors, such as pump 100.

To address this need and to enable suction detection in such blood pumps that do not include pressure sensors, the present disclosure describes systems and methods for detecting suction events in blood pumps using solely the motor current signal of the pump. In one aspect, a system and method are disclosed for detecting suction events using a pulsatility index of the motor current signal. In another aspect, a system and method are disclosed for detecting suction events using an index of a normalized band-pass filtered signal of the motor current signal. In yet another aspect, a system and method are disclosed for detecting suction events using both the pulsatility index and the index of the normalized band-pass filtered signal.

The suction detection methods described herein (i.e., methods 600, 1100, 1200, described below) may be implemented in control until 200 of pump system 100. For example, computer-readable instructions for one or all of the methods described below may be stored in the one or more memory 202 and executed by the one or more processors 204 of control unit 200 during use of the pump to detect suction events. Moreover, the parameters and settings of the one or more processors used in the methods described herein, such as the predetermined thresholds, the predetermined window lengths, the bins sizes, and/or any other parameters and settings of the methods described below may be stored in memory 202. The parameters and settings and which particular suction detection method executed by the processor 204 may be adjusted or selected by the user via user input to user interface 206 of control unit 200.

Normalization.

Figure 3:
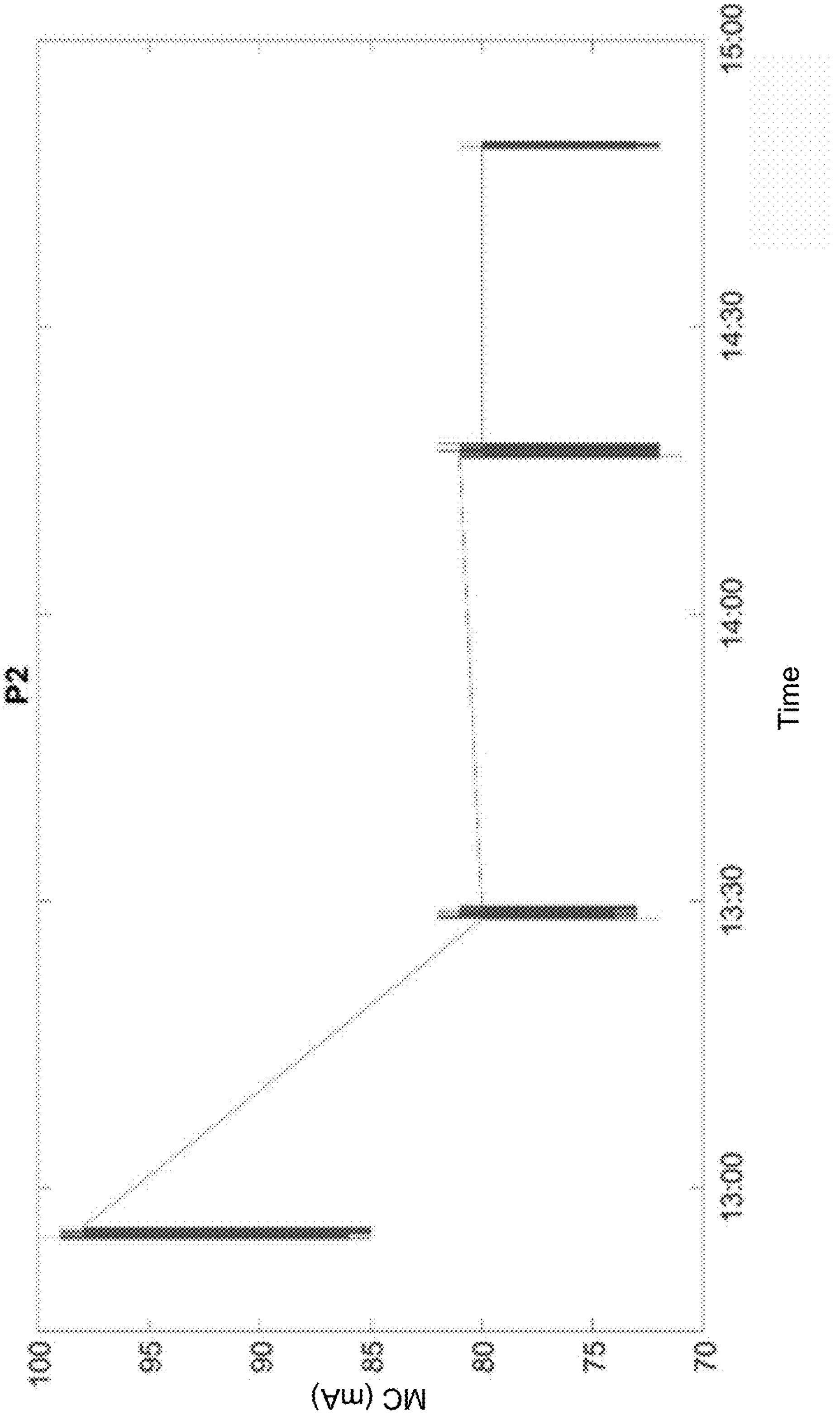
FIG. 3 is a graph of a motor current signal of a pump in accordance with the present technology.

During normal usage of pump 100 and absent the occurrence of a suction event, the motor current of motor 150 may vary over time, such as by trending downward with the passage of time. For example, a downward trending motor current is shown in FIG. 3 in accordance with the methods described herein. In the graph of FIG. 3, the y-axis represents motor current (in mA) and the x-axis represents time. Thus, the downward trending motor current makes it challenging to achieve absolute thresholds that can be reliably implemented in a processor configured to detect suction events. Moreover, there is variability in the characteristics and performance of different pump models and the speed of operation for those different pumps. Therefore, as will be described in more detail below, in some aspects, the indexes of the processor outputs that are provided by the methods described herein may be normalized and do not rely on the absolute value of the motor current. Using normalized indexes produces more reliable suction detection by incorporating absolute or global thresholds used to detect suction events that may be used with different pumps, across different pump speeds, and in view of the varying (e.g., decreasing) motor current.

Suction Detection Using Pulsatility Index.

In one aspect of the present technology, a pulsatility index is used to detect a suction event in a pump system, such as pump system 100. For example, in the field of medical ultrasound analysis of blood flow, the pulsatility index is defined as the difference between peak systolic and end-diastolic blood flow velocity, divided by the time-averaged flow velocity. Such a pulsatility index is postulated to reflect the vascular resistance in the arteries distal from the location of acoustic insulation. As described herein, the principles of the systolic and diastolic flow velocity pulsatility may be extended to the motor current signal of a blood pump to calculate a pulsatility index (PI) of the motor current and are used to detect suction events.

For example, in one aspect of the present technology, to calculate the PI of the motor current signal, the maximum motor current (max MC) and the minimum motor current (min MC) within a predetermined time duration window (predetermined window) are each detected by the processor 204. Also, the mean motor current (mean MC) is calculated by the processor 204 by averaging the motor current samples within the predetermined window:

$$\text{mean } MC = \sum_{i=0}^{N} \frac{MC(i)}{N} \quad \text{(Equation 1)}$$

where N represents the number of samples collected in the predetermined time window. In one aspect, the predetermined window is 2 seconds and the number of samples N collected in the predetermined time window is 500. The 2 second time window is selected to provide a balance between sensitivity and stability when used to detect a suction event using the algorithms of the present technology. In this regard, a 2 second time window is sufficiently short to enable the method to be sensitive enough to detect a suction event, while also being sufficiently long to enable the method to be stable. It is to be appreciated that other time durations less than or greater than 2 seconds (e.g., 1 second, 5 second, etc.) for the predetermined window are contemplated to be within the scope of the methods described herein.

With the max MC, min MC, and mean MC now calculated, the processor 204 calculates a normalized PI of the motor current signal as defined below:

$$PI = \frac{(\max MC) - (\min MC)}{\text{mean } MC} \quad \text{(Equation 2)}$$

Figure 4:
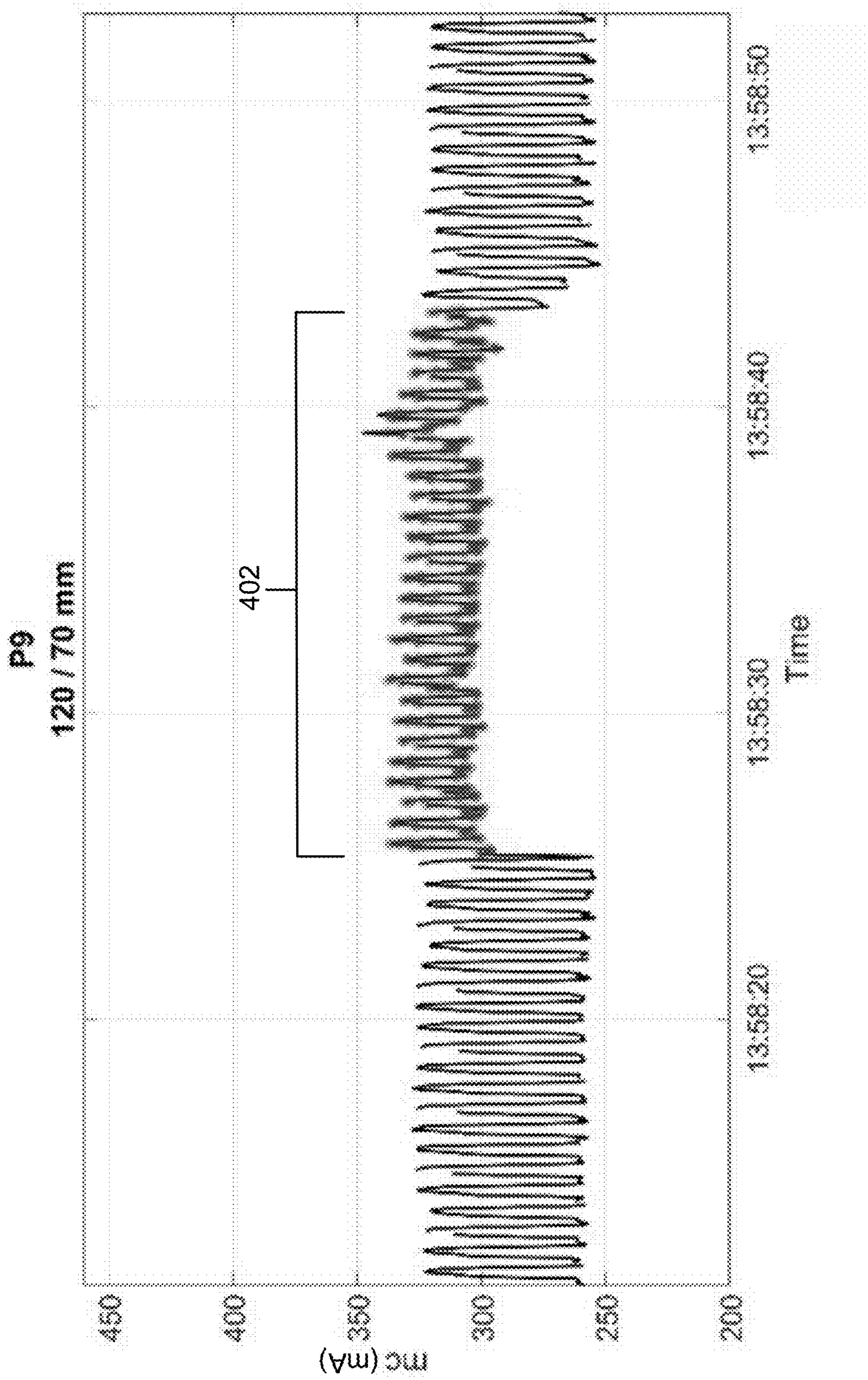
FIG. 4 is a graph illustrating pulsatility in a motor current signal of a pump in accordance with the present technology.

When a suction event occurs, it causes the PI of the motor current to decrease and the minimum motor current to increase. For example, this effect is shown in the graph of FIG. 4 in accordance with the present technology. In FIG. 4, the y-axis represents motor current measured in mA and the x-axis represents time. As shown, during use of the pump, the motor current exhibits pulsatile behavior. However, the pulsatility of the motor current during a suction event is altered. In this regard, as shown in FIG. 4, during a suction event 402, the PI (as calculated in Equation 2) of the motor current is decreased and the min motor current is increased relative to the PI and minimum motor current outside (before and after) the suction event 402.

Figure 5:
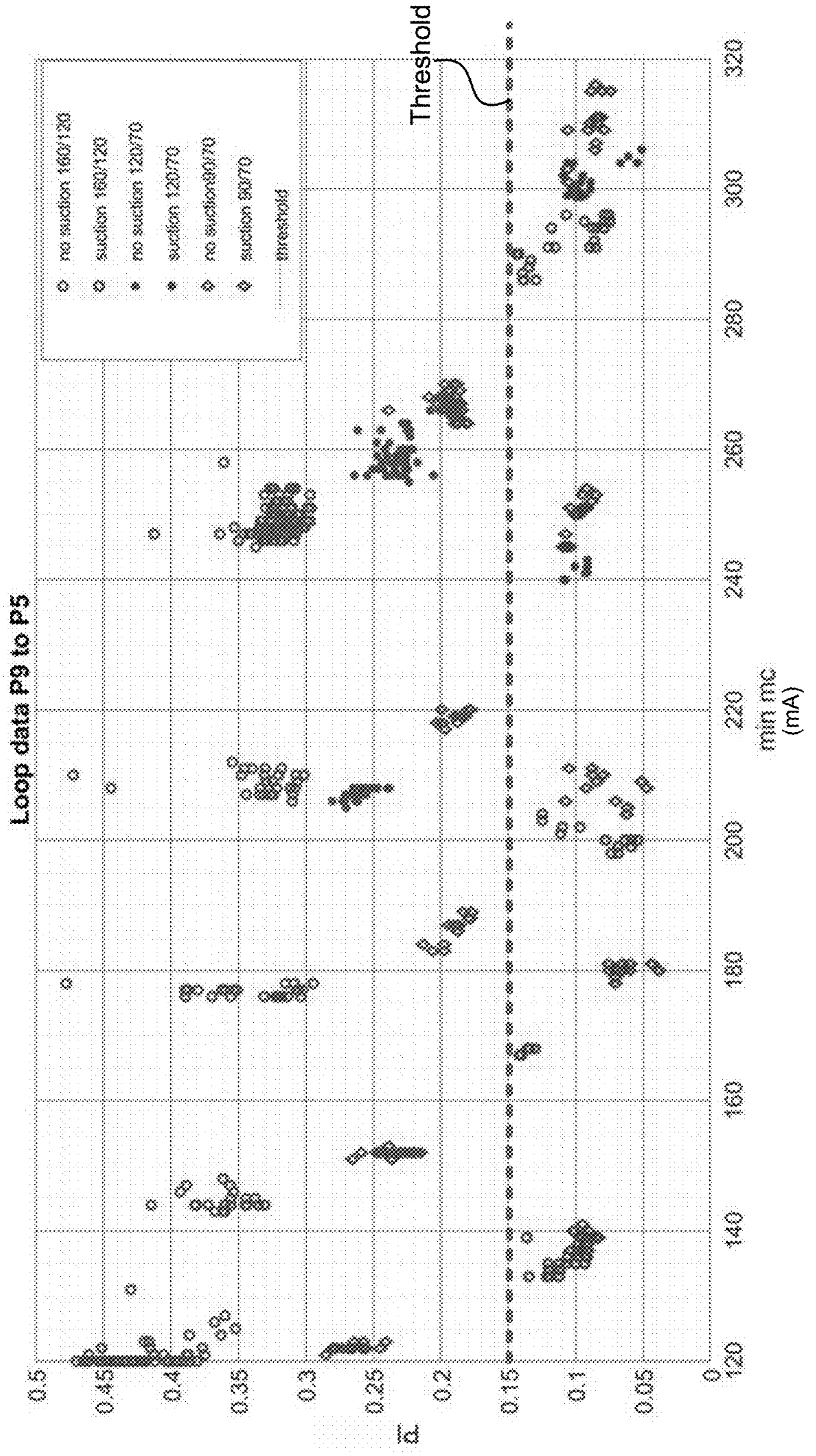
FIG. 5 is a graph illustrating suction detection with respect to a pulsatility index threshold in accordance with the present technology.

The decrease in pulsatility of the motor current exhibited during a suction event is used in accordance with the present technology to detect such suction events during use of the pump. Since, the calculated PI is normalized, a global threshold can be defined across all pump speeds and in view of the decreasing motor current over time. The global threshold may then be compared to a calculated PI of the motor current when the pump is in use to detect if a suction event is occurring. For example, in one aspect, the threshold may be approximately (e.g., +/−10%) 0.15. Referring to FIG. 5, a graph is shown in accordance with the present technology of the results of lab testing, where different pump speeds (represented as p-levels P9 to P5 in FIG. 5) and blood pressure conditions (i.e., 90/70, 120/70, 160/20 mmHg shown in the legend of FIG. 5) both during a suction event and absent a suction event were simulated. In the graph of FIG. 5, the y-axis represents PI of the motor current and the x-axis represents the minimum motor current (measured in mA) of the pump motor. As shown in FIG. 5, when there was no suction event present, the calculated PI was above 0.15 and, when there was a section event present, the calculated PI was below 0.15. Thus, 0.15 was found to be a suitable PI for predicting the occurrence of a suction event under different pump speeds and blood pressure conditions. A threshold of 0.15 is found to balance sensitivity with stability or specificity when used in detecting a suction event. It is to be appreciated that other threshold values for comparison with the calculated PI are contemplated to be within the scope of the present disclosure.

Figure 7:
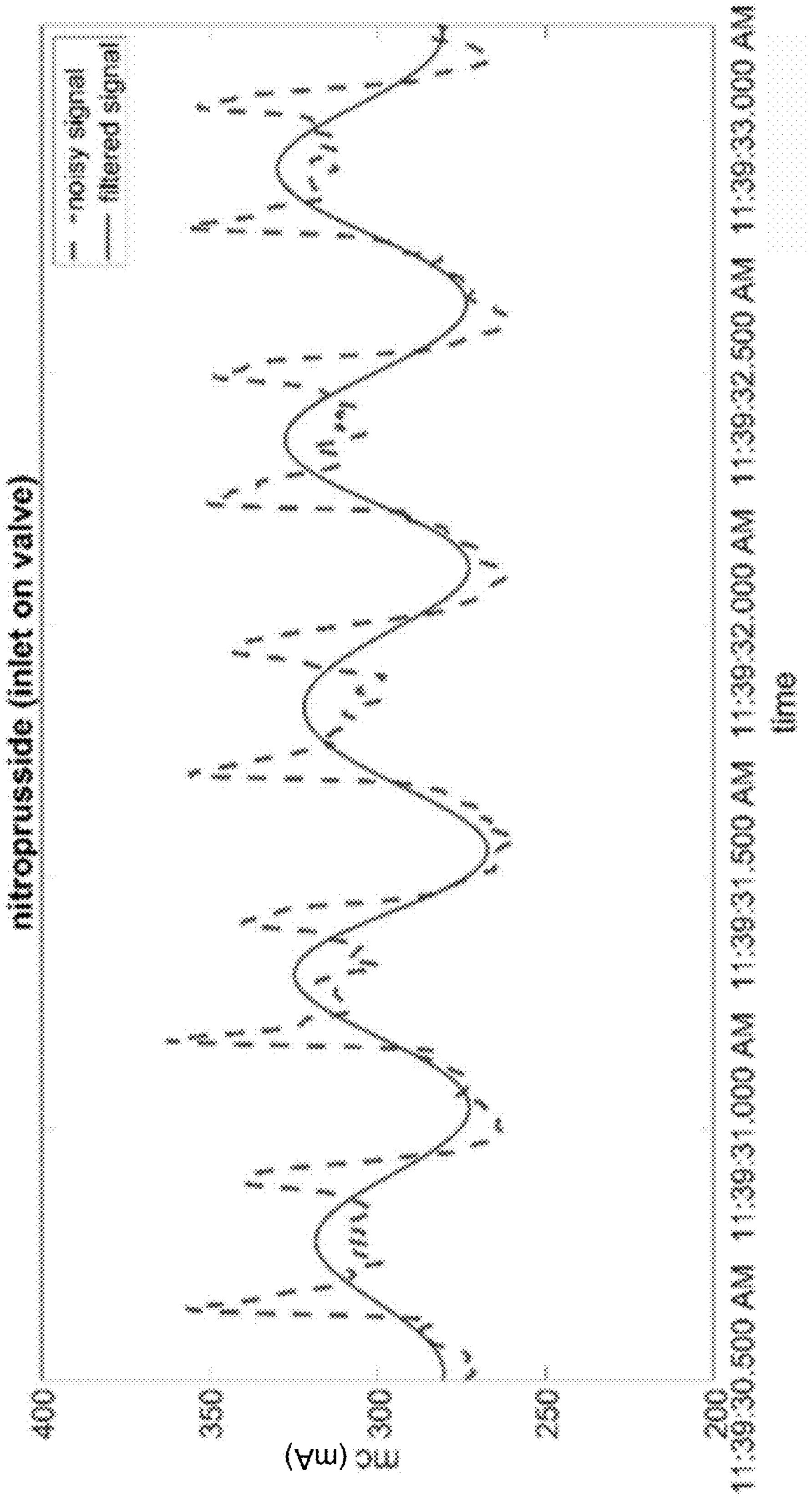
FIG. 7 is a graph illustrating a noisy motor current signal and a filtered motor current signal in accordance with the present technology.

Referring to FIG. 7, a graph of a motor current signal and a filtered motor current signal is shown in accordance with the present technology. The results in the graph of FIG. 7 were obtained during an animal study in a noisy environment. The y-axis represents motor current measured in mA and the x-axis represents time. The dotted line of the graph in FIG. 7 is the motor current signal. As shown, in noisy environments, the motor current signal includes spikes and noise that may reduce the accuracy of the method described above using the PI of the motor current. The signal may be filtered, as shown in the solid line of FIG. 7, to produce a less noisy and smoother signal that can increase the accuracy of the suction detection methods. For example, the motor current signal may be low-pass filtered using a 15 Hz low-pass filter that is selected to remove the noisy spikes in the motor current signal while also preserving the relevant pulsatility and heart beat information in the signal.

Figure 6:
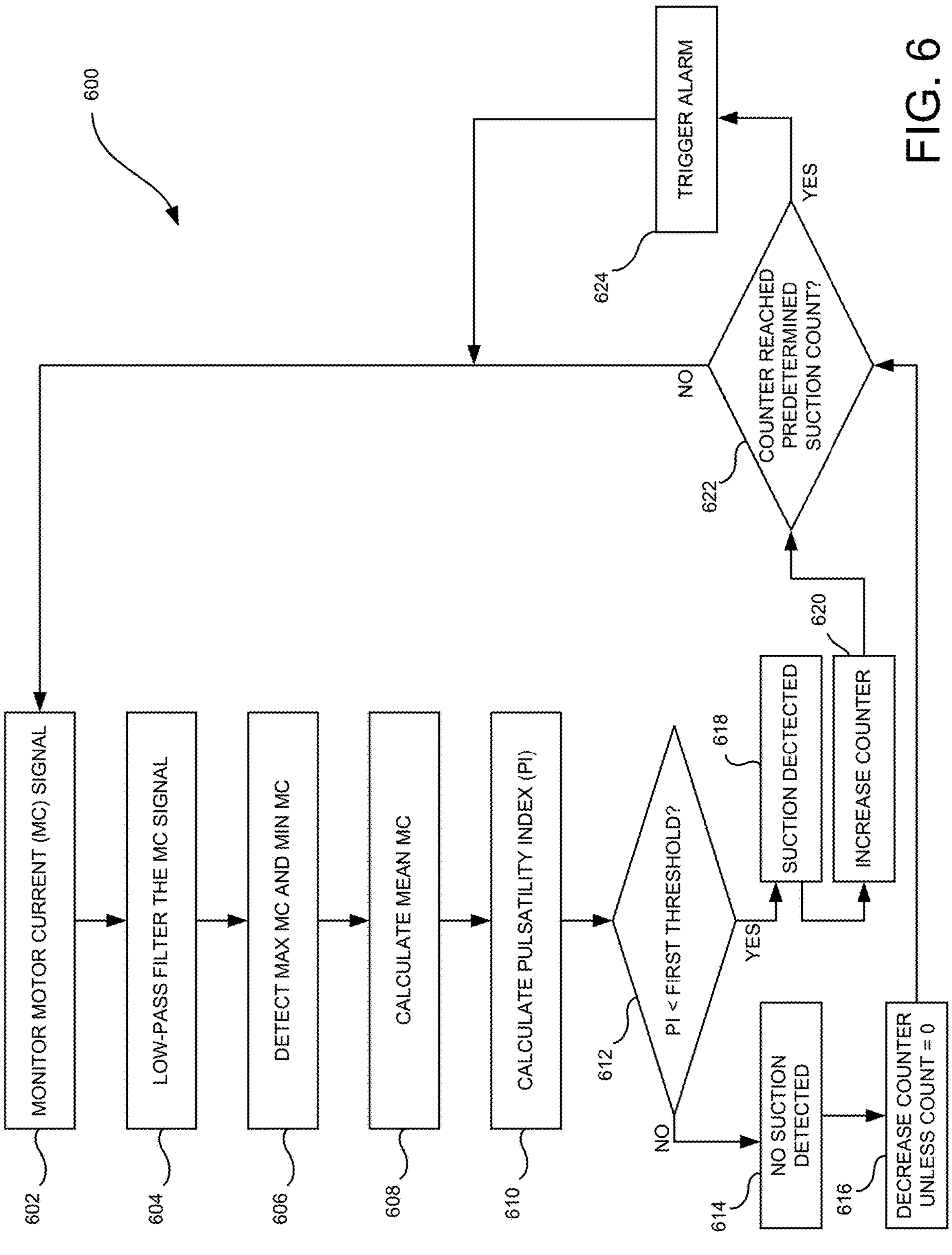
FIG. 6 is a flow chart of a method for detecting suction events in accordance with the present technology.

Referring to FIG. 6, a method 600 for detecting a suction event using the PI of the motor current during usage of a pump in a patient, such as pump 100, is shown in accordance with the present technology. It is to be appreciated that method 600 may be performed or executed by one or more processors of the pump system, such as processor 204, using the motor current of the pump as the only input.

Figure 9:
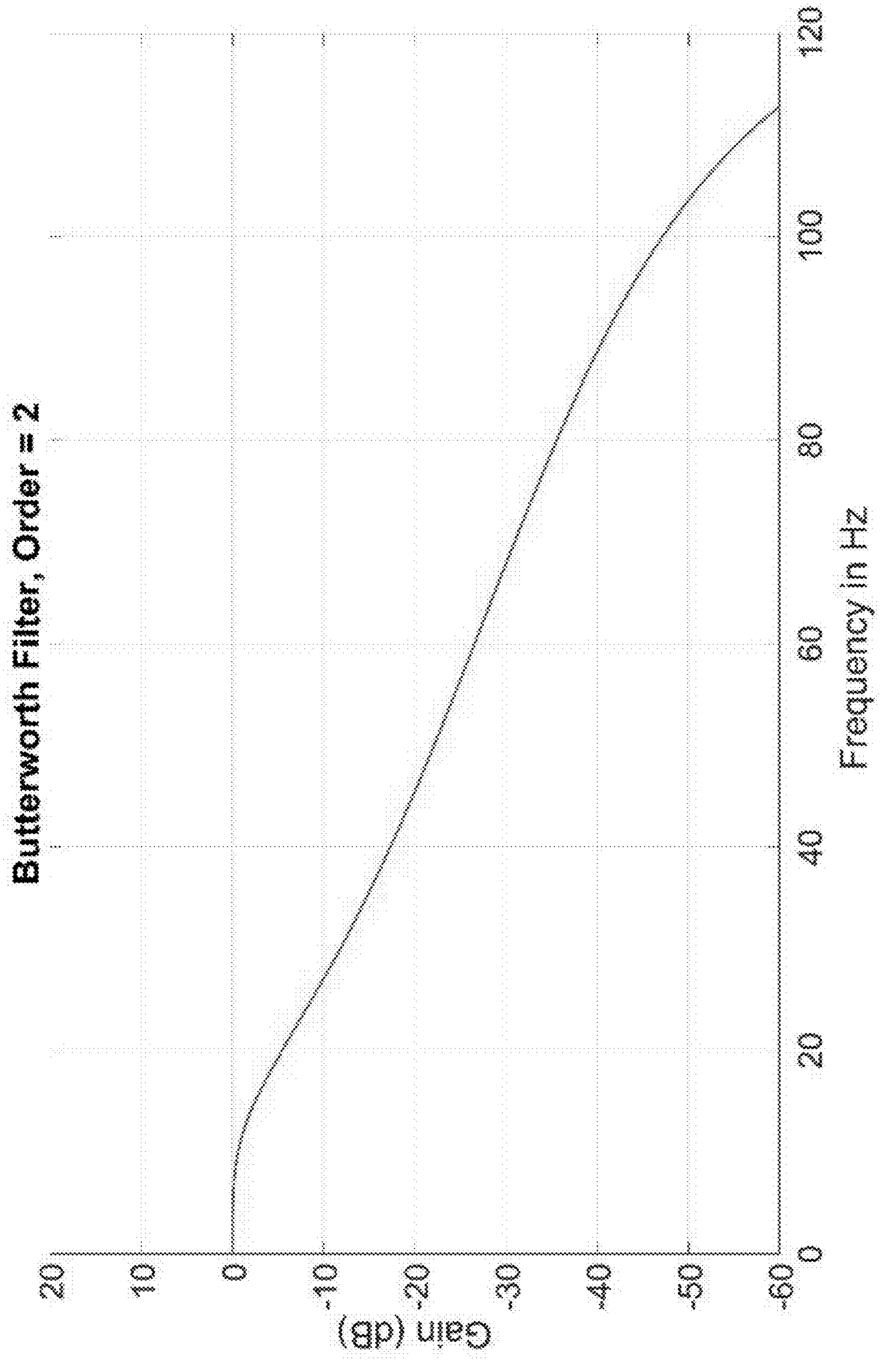
FIG. 9 illustrates a filter response of a Butterworth filter in accordance with the present technology.

Initially, in step 602, the processor 204 monitors the motor current of the pump motor after deployment of the pump into the patient and activation of the pump. In step 604, the motor current signal is filtered using a low-pass filter to remove noise and spikes from the motor current signal. For example, in one aspect, a 15 Hz low-pass filter may be used to filter the motor current signal, though it should be appreciated that other low-pass filters may be suitable in other aspects (e.g., low-pass filters based on frequencies other than 15 Hz). In one exemplary aspect, the low-pass filter may be a second-order Butterworth Filter as shown in FIG. 9. Moreover, it is to be appreciated that the filtering may be implemented digitally by processor 204. Alternatively, processor 204 may control an analogue filter circuit, for example, included in control unit 200 or external to control unit 200 to low-pass filter the motor current signal.

In step 606, processor 204 detects the max MC and the min MC within a predetermined time window (e.g., two seconds) of the filtered motor current signal. In step 608, processor 204 calculates the mean MC of the motor current samples in the predetermined window of the filtered motor current signal in accordance with Equation 1 above. In step 610, processor 204 calculates the PI of the motor current for the predetermined window using the detected max MC and min MC of step 606 and the calculated mean MC of step 608 in accordance with Equation 2 above. In step 612, processor 204 compares the calculated PI of step 610 to a first threshold. As described above, the first threshold may be approximately 0.15 and may be reliably used across different pump speeds, different pump types, and in view of the down-trending motor current. If, in step 612, processor 204 determines that the calculated PI is not below (i.e., it is above) the first threshold, the processor 204 determines that no suction is detected in step 614. Alternatively, if, in step 612, processor 204 determines that the calculated PI is below the first threshold, processor 204 determines that a suction is detected in step 618.

In one aspect, suction detection method 600 may include a counter (implemented and maintained by processor 204 and stored in memory 202) that keeps a count of no suction/suction detections from steps 614, 618. For example, in one aspect, the counter is a stepwise counter such that processor 204 decreases the counter by 1 if no suction is detected and increases the counter by 1 if suction is detected. It is to be appreciated that if the counter is at 0, the processor 204 will not decrease the counter to below 0, i.e., 0 is the floor of the counter. If the processor 204 determines that the counter has reached a predetermined suction count, an alarm condition is triggered by the processor 204. The predetermined suction count is selected to balance sensitivity with stability of the suction detection. In this regard, the predetermined suction count may prevent false positives by requiring several clustered confirmations of the comparison at step 612 to trigger an alarm condition for indicating that a suction event is occurring. In one aspect, the predetermined suction count is set to 4, however, the predetermined suction count may be set to more or less than 4 in accordance with the present disclosure. In one aspect, the predetermined suction count may be adjustable by a user via user input, e.g., to user interface 206.

For example, returning to method 600 in FIG. 6, when no suction is detected based on the comparison at step 612, processor 204 decreases or decrements the counter by 1 in step 616. Alternatively, when suction is detected based on the comparison at step 612, processor 204 increases or increments the counter by 1 in step 620. As described above, if the counter is at 0, the processor 204 will not decrease the counter to below 0, i.e., 0 is the floor of the counter. In step 622, processor 204 determines if the counter has reached a predetermined suction count. If, in step 622, processor 204 determines that the counter has not reached the predetermined suction count, processor 204 returns to monitoring the MC signal in step 602 and method 600 is executed again. Alternatively, if, in step 622, processor 204 determines that the counter has reached the predetermined suction count, processor 204 triggers an alarm condition in step 620 to alert the user of the pump 100 that a suction event has been detected and processor 204 resets the counter to 0. The alarm condition may comprise triggering one or more indicators for alerting a user of the detected alarm condition. For example, the indicators may include light indicators (e.g., light-emitting diodes (LEDs), audible alarms, and/or notifications or messages outputted for display to a display device, e.g., in user interface 206 of control unit 200. The light indicators and/or speakers for outputting the audible alarms may be included in user interface 206 control unit 200. The indicators may further include vibration or haptic actuators (e.g., in the handle of pump 100 to alert the user via haptic feedback). The indicators may include one of the light indicators, audible alarms, haptic actuators and notifications, or a combination or sub-combinations of such indicators. After triggering the alarm condition and resetting the counter to 0 in step 624, the processor 204 then returns to monitoring the MC signal in step 602 of method 600.

It is to be appreciated that, although a stepwise counter is described above for use in method 600, in other aspects of the present technology, other types of counters may be used for triggering the alarm condition. For example, in one aspect, processor 204 may control or maintain a counter (e.g., stored in memory 202) that keeps a count of a number of previous windows (e.g., a two second window, as described above) of the filtered motor current signal that have been determined by processor 204 to include an indication of suction (detected in step 618 based on the comparison in step 612). If processor 204 determines that a predetermined number of windows of a predetermined total number of previous windows (e.g., 4 out of the 7 previous windows, 5 out of 8 previous windows, or another ratio) includes an indication of suction, the processor 204 determines a suction event has occurred and triggers the alarm condition.

In one aspect of method 600, steps 614 and 618 may be removed and, in this aspect, processor 204 may determine that a suction event has occurred only if the predetermined suction count at step 622 has been reached.

In another aspect of method 600, steps 616, 620, and 622 (the steps relating to the counter) may be removed from the method 600 and, in this aspect, processor 204 triggers the alarm condition if a suction is detected in step 618 (based on the comparison at step 612) and returns to monitoring the motor current in step 602. If processor 204 does not detect a suction condition in step 614, the method returns to monitoring the motor current in step 602.

Suction Detection Using Normalized Minimum Bandpass Signal.

Another aspect for suction detection will now be described that includes additional signal filtering. For example, in this second aspect, in addition to low-pass filtering the motor current (MC) signal (e.g., using a 15 Hz low-pass filter, as described above), the motor current signal is further filtered by processor 204 using a band-pass filter that passes frequencies in a second predetermined range, such as, 0.5 to 5 Hz. The second predetermined range, e.g., 0.5 to 5 Hz, is selected based on the typical heart beat frequency range of 30 to 300 beats per minute (BPM). It is to be appreciated that the second predetermined range may be 0.5 to 3 Hz, 0.5 to 5 Hz, 0.5 to 8 Hz, 0.5 to 10 Hz, or any other suitable range that contains sufficient information regarding the pulsatility of the heartbeat of the patient. A range of 0.5 Hz to 5 Hz may balance sensitivity with stability when used in this aspect of suction detection described in more detail below.

The band-pass filtering is analogous to extracting pulsatility information from the motor current signal assuming the typical heartbeat range of 30 to 300 BPM. The band-pass and low-pass filters may be digital filters (e.g., filter software that may be stored in memory 202 and executed by processor 204) applied by processor 204. Alternatively, processor 204 may control analogue filter circuits (including suitable low-pass and a band-pass filters), for example, included in control unit 200 or external to control unit 200, to low-pass filter and band-pass filter the motor current signal.

Figure 8:
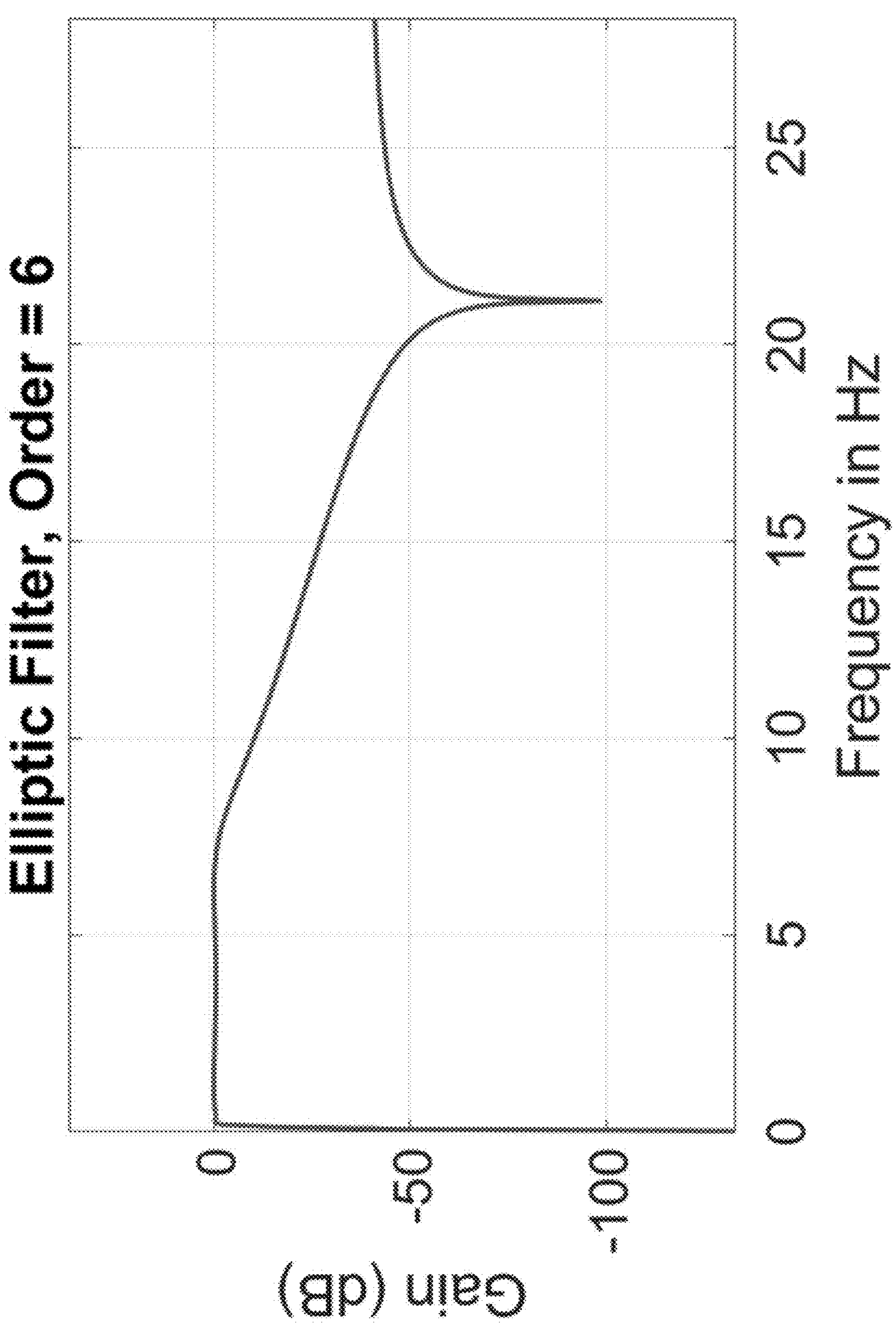
FIG. 8 illustrates a filter response of an elliptic filter in accordance with the present technology.

In one aspect, the band-pass filter may be a sixth-order elliptic filter that passes frequencies in the second predetermined range, e.g., 0.5 to 5 Hz. FIG. 8 illustrates a graph of the filter response of such an elliptical filter, where the y-axis represents the gain (in dB) and the x-axis represents the frequency (in Hz) of the elliptical filter that passes through all frequencies ranging from 0.5 to 5 Hz. Moreover, in one aspect, the low-pass filter may be a second-order Butterworth filter that passes frequencies in the first predetermined range, e.g., 0 Hz to 15 Hz. FIG. 9 illustrates a graph of the filter response of such a Butterworth filter, where the y-axis represents the gain (in dB) and the x-axis represents the frequency (in Hz) of the Butterworth filter that passes through all frequencies ranging from 0 to 15 Hz.

As described above, normalization of the signals used in the suction detection methods allows the use of absolute thresholds to detect suction events even though the motor current may vary (e.g., trend downward) over time. Thus, this aspect of the methods described herein continues by normalizing the band-pass filtered signal. For example, in one aspect, the processor 204 normalizes the band-pass signal according to the following equation:

$$\text{normalized bandpass filtered signal} = \frac{MC(bandpass(i))}{MC(lowpass(i))} \quad \text{(Equation 3)}$$

$$i = 0 \text{ to } N$$

where, Equation 3 is performed as a point-by-point operation such that each sample i of the band-pass filtered signal (MC(bandpass(i)) in Equation 3) is divided by each sample i of the low-pass filtered signal (MC(lowpass(i)) in Equation 3) to generate the normalized band-pass signal.

Figure 15:
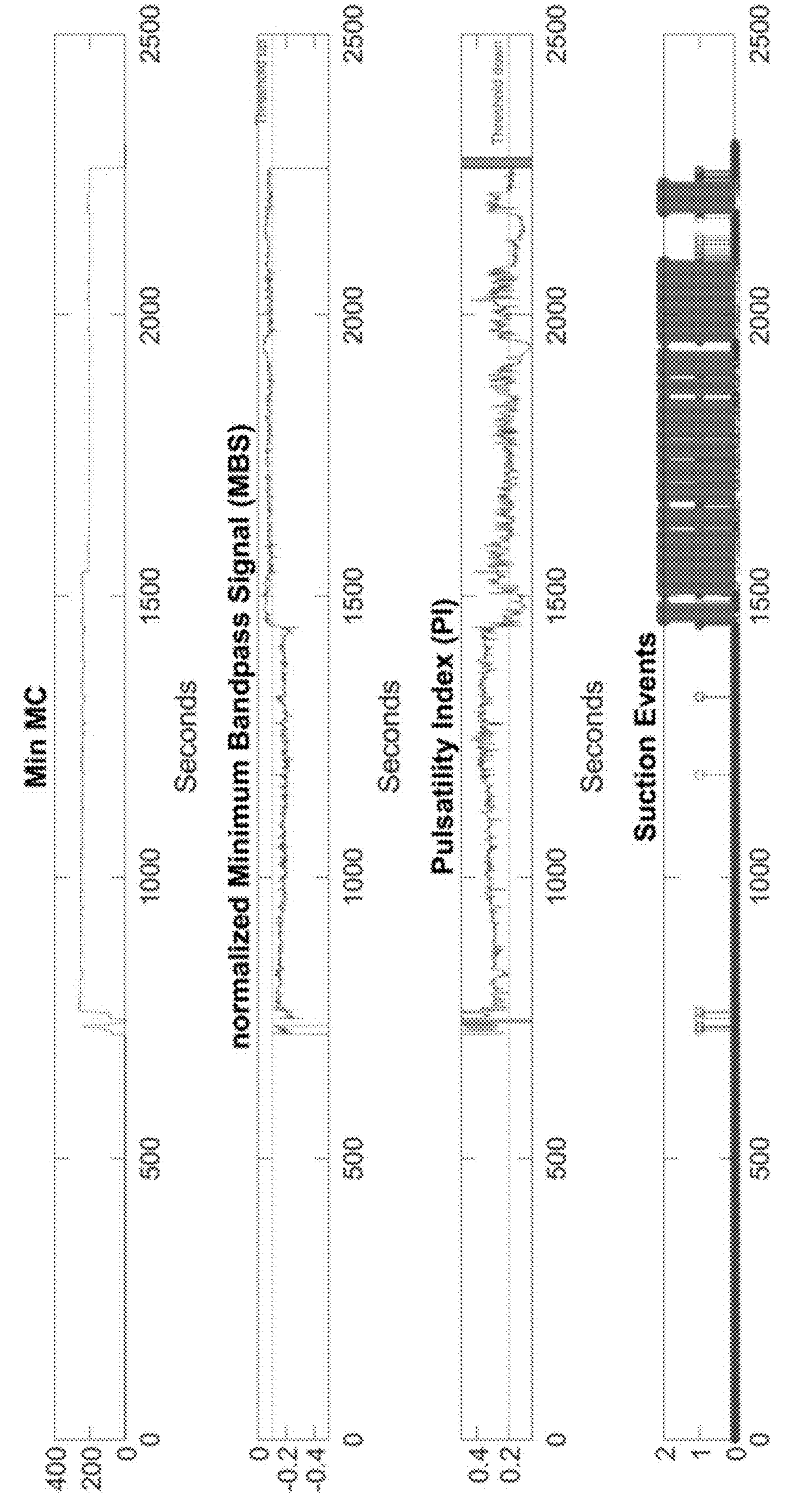

The processor 204 then calculates a normalized minimum band-pass signal index (herein referred to as the MBS index) by detecting a minimum value of the normalized band-pass filtered signal within a predetermined window of the signal and evaluating the MBS index relative to a threshold. In one aspect the absolute value of the detected minimum value within the predetermined window (i.e., abs(MBS)) is compared to the threshold value. Using the absolute value of MBS makes the determination of suction events more straightforward. Referring to FIG. 15, in the bar graph for normalized Minimum Bandpass Signal (MBS), values greater than the threshold are indicia of a suction event. Because the current represented by MBS may be negative, values that are "more negative" (i.e., smaller, but larger than threshold in the absolute value sense) are indicia of "no suction." Using the absolute value of these negative values, the absolute value of the MBS values that are below threshold are indicia of suction events and abs(MBS) values above threshold are indicia of no suction. The predetermined window for MBS calculation may be 2 seconds, which is a window that may balance reliability and stability of the suction detection, as described above. However, other windows (e.g., 1 second, 3 seconds, 4 seconds, 5 seconds, etc.) are contemplated herein. Since the normalized band-pass filtered signal is normalized, a second predetermined threshold can be defined across different pump speeds, pump types, and in view of a varying (e.g., decreasing) motor current over time. The second predetermined threshold may then be compared to the abs(MBS) value of the normalized band-pass filtered motor current signal when the pump is in use to detect if a suction event has occurred. For example, in one aspect, the second threshold may be approximately (e.g., +/−10%) 0.07, wherein an abs(MBS) value below the second threshold is indicative of the occurrence of a suction event and an abs(MBS) value above the second threshold is indicative of the absence of a suction event. A second threshold of 0.07 is found to balance sensitivity with stability when used to detect a suction event. It is to be appreciated that other threshold values for comparison with abs(MBS) are contemplated herein. For example, the second threshold may be in a range of 0.05 to 0.12. It is to be appreciated that values in the lower end of this range may result in increased sensitivity but decreased stability when used as the second threshold for comparison to abs(MBS). Moreover, values at the higher end of this range may result in decreased sensitivity but increased stability when used as the second threshold for comparison to abs(MBS).

Figure 10:
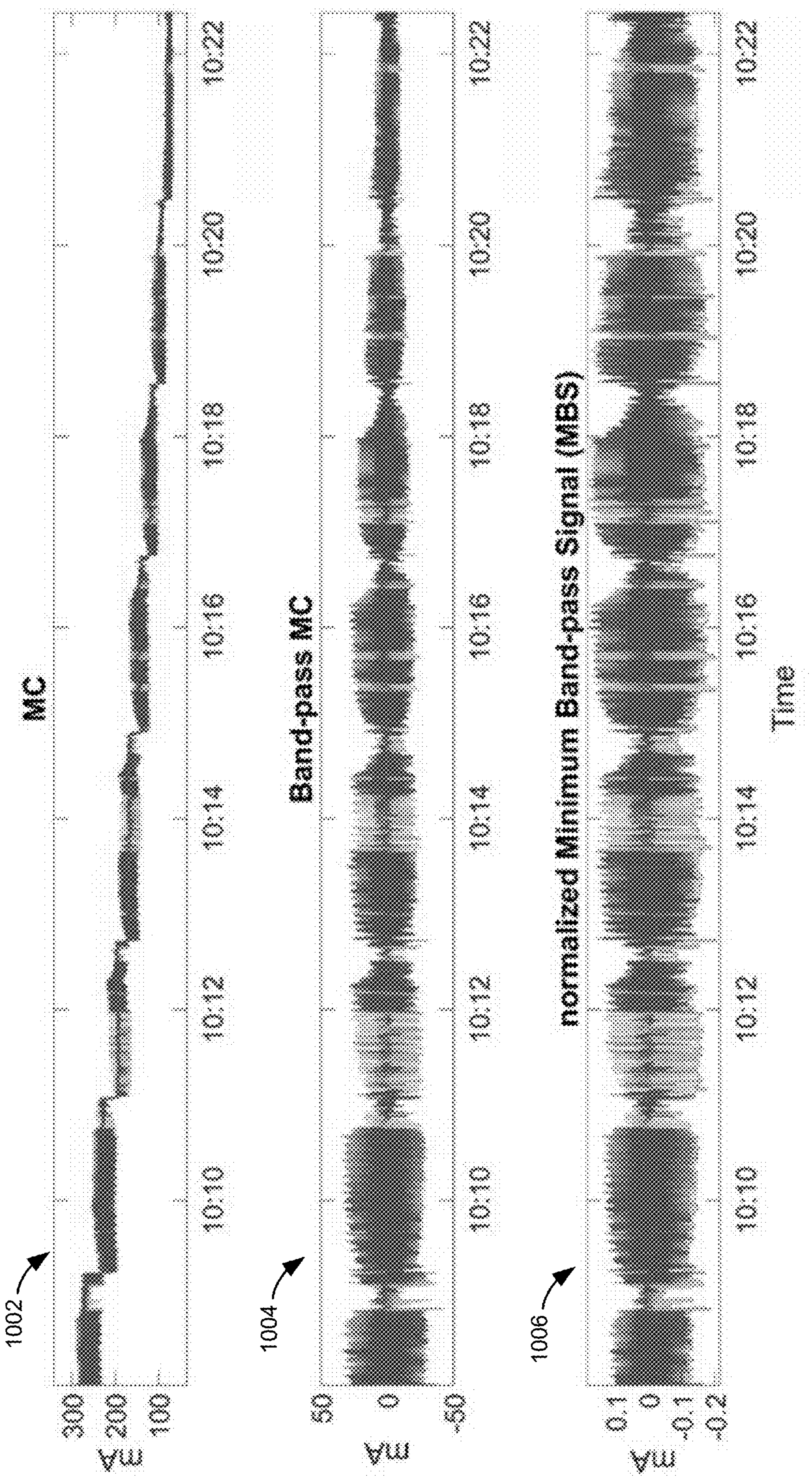
FIG. 10 illustrates filtering and normalization of a motor current signal of a pump in accordance with the present technology.

The process of filtering and normalizing the motor current signal, described above, is shown in FIG. 10 in accordance with the present technology. For example, FIG. 10 includes graphs 1002, 1004, 1006, where the y-axis of each graph is motor current (in mA) and the x-axis of each graph is time (marked in 2-second increments). Graph 1002 shows the motor current of the pump, graph 1004 shows the motor current signal of graph 1002 after being low-pass filtered using the Butterworth filter described above and band-pass filtered using the elliptic filter described above, graph 1006 shows the band-pass filtered signal after being normalized in accordance with Equation 3 above. The original motor current signal in graph 1002 was obtained during an animal study where the motor speed was controlled in a stepwise fashion (as shown in the stepwise motor current change). At the end of each speed change, a suction event was simulated with inferior vena cava (IVC) occlusion (using an occlusion tool, as described below) and/or placing the inlet of the pump near the aortic valve. The simulated suction events can be seen in the spaced narrowing of the signals in graphs 1004 and 1006 where the motor current pulsatility decreases during each suction event. As shown in graph 1006, by normalizing the band-pass filtered signal, the filtered signal in graph 1006 obtains a more uniform shape even if view of the changing motor speed during the experiment. Thus, the different pulsatilities of the band-pass filtered signal shown in graph 1004 have been normalized for comparison against the second threshold described above. In this regard, the minimum value of the normalized band-pass signal shown in graph 1006 is detected in every 2 second window and the absolute value of the minimum value (i.e., the calculated MBS index) is compared against the second threshold value to determine if a suction event occurred/is occurring in the window evaluated.

Figure 11:
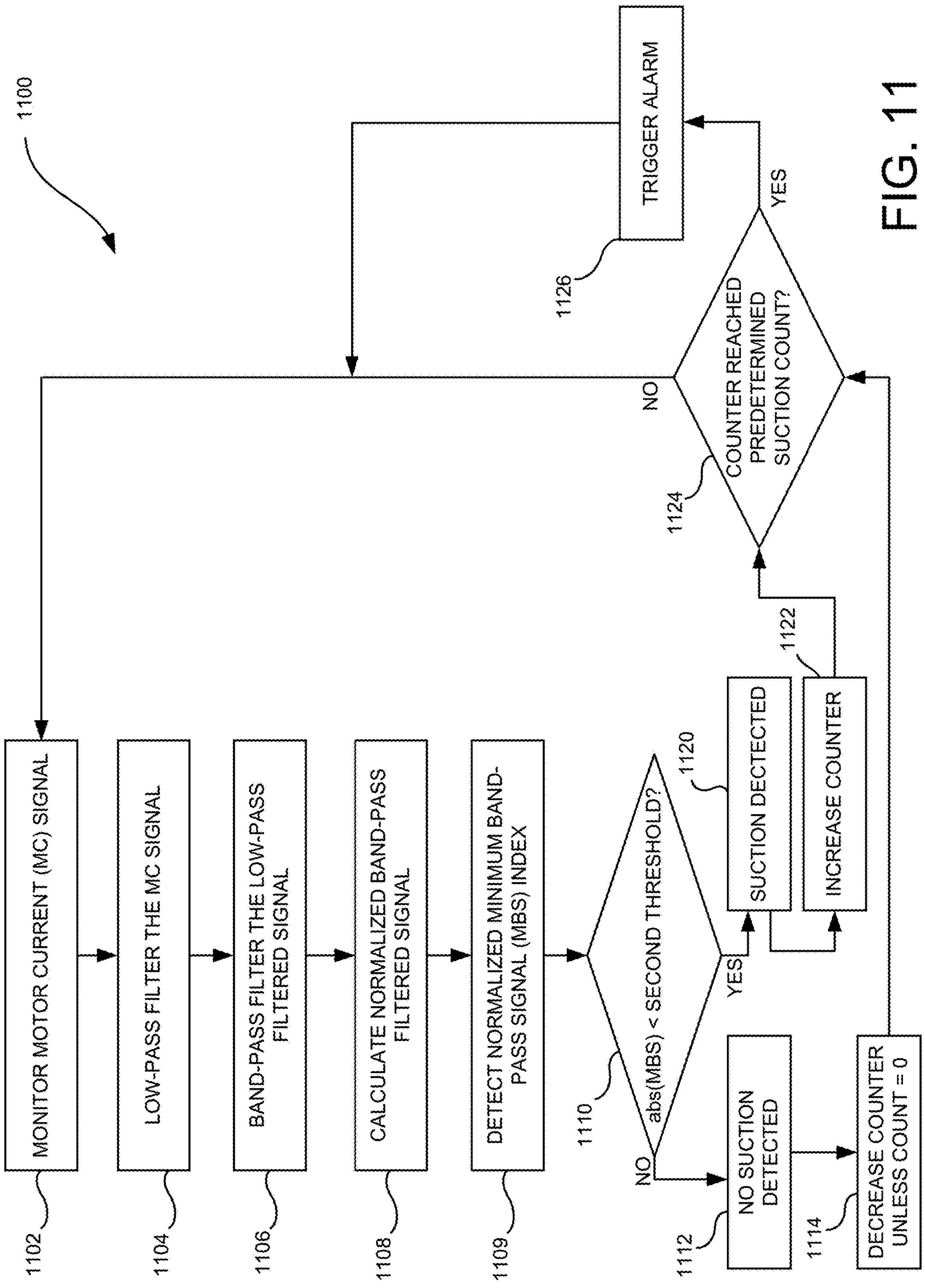
FIG. 11 is a flow chart of another method for detecting suction events in accordance with the present technology.

Referring to FIG. 11, a method 1100 for detecting a suction event using the above-described band-pass filtering, normalization, and MBS index value during usage of a pump in a patient, such as pump 100, is shown in accordance with the present technology. It is to be appreciated that method 1100 may be performed or executed by one or more processors of the pump system, such as processor 204 of pump 100, using the motor current of the pump as the only input.

Initially, in step 1102, the processor 204 monitors the motor current of the pump motor after deployment of the pump into the patient and activation of the pump. In step 1104, the motor current signal is filtered using a low-pass filter. For example, in one aspect, a 15 Hz low-pass filter, such as the second-order Butterworth Filter described above, may be used to filter the motor current signal. In step 1106, the low-pass filtered signal is band-pass filtered by processor 204 using a band-pass filter that passes frequencies of the signal in a predetermined range, such as, 0.5 to 5 Hz, as described above. For example, in another aspect, a sixth-order elliptic filter that passes frequencies ranging from 0.5 Hz to 5 Hz may be used to filter the low-pass filtered signal, as described above.

It is to be appreciated that the filtering in method 1100 may be implemented digitally by processor 204. Alternatively, processor 204 may control analogue filter circuits (including suitable low-pass and a band-pass filters), for example, included in control unit 200 or external to control unit 200, to low-pass filter and band-pass filter the motor current signal.

In step 1108, processor 204 calculates the normalized band-pass filtered signal of the band-pass signal by dividing each sample of the band-pass filtered signal of step 1106 with each corresponding sample of the low-pass filtered signal of step 1104 in accordance with Equation 3 above. In step 1109, processor 204 calculates the MBS index of the normalized band-pass filtered signal by detecting the minimum value within a predetermined time window (e.g., two seconds) of the normalized band-pass filtered signal and determines abs(MBS) from the calculated value. In step 1110, processor 204 compares the abs(MBS) of step 1109 to a second threshold. As described above, the second threshold may be 0.07 and may be reliably used across different pump speeds, pump types, and in view of varying (e.g., down-trending) motor current. If, in step 1110, processor 204 determines that abs(MBS) is not below (i.e., it is equal to or above) the second threshold, the processor 204 determines that no suction is detected in step 1112. Alternatively, if, in step 1110, processor 204 determines that abs(MBS) is below the second threshold, processor 204 determines that a suction event is detected in step 1120.

As described above, a counter may be implemented by processor 204 to balance the reliability and stability of the suction detection. The counter may be a stepwise counter or any other suitable counter, as described above.

For example, returning to method 1100 in FIG. 11, when no suction is detected based on the comparison at step 1110, processor 204 decreases or decrements the counter by 1 in step 1114. Alternatively, when suction is detected based on the comparison at step 1110, processor 204 increases or increments the counter by 1 in step 1122. As described above, if the counter is at 0, processor 204 will not decrease the counter to below 0, i.e., 0 is the floor of the counter. In step 1124, processor 204 determines if the counter has reached a predetermined suction count. If, in step 1124, processor 204 determines that the counter has not reached the predetermined suction count, processor 204 returns to monitoring the MC signal in step 1102 and method 1100 is executed again. Alternatively, if, in step 1124, processor 204 determines that the counter has reached the predetermined suction count, processor 204 triggers an alarm condition in step 1126 to alert the user of the pump 100 that a suction event has been detected and processor 204 resets the counter to 0. The alarm condition may comprise triggering one or more indicators for alerting a user of the detected alarm condition as described above in relation to step 624 of method 600. After triggering the alarm condition and resetting the counter to 0 in step 1126, the processor 204 then returns to monitoring the MC signal in step 1102 of method 1100.

In another aspect of method 1100, steps 1112 and 1120 may be removed and, in this aspect, processor 204 may determine that a suction event has occurred only if the predetermined suction count at step 1124 has been reached.

In another aspect of method 1100, steps 1114, 1122, and 1124 (the steps relating to the counter) may be removed from the method 1100 and, in this aspect, processor 204 triggers the alarm condition if a suction event is detected in step 1120 (based on the comparison at step 1110) and returns to monitoring the motor current in step 1102. If processor 204 does not detect a suction condition in step 1112, the method returns to monitoring the motor current in step 1102.

Suction Detection Using Both PI and MBS Index.

In one aspect, the algorithms using the PI of the motor current and the MBS index described above in relation to FIGS. 6 and 11, are combined according to another aspect of the methods described herein. The combination of the PI and MBS index in a single method may produce even more sensitive and stable results for suction detection.

Figure 12:
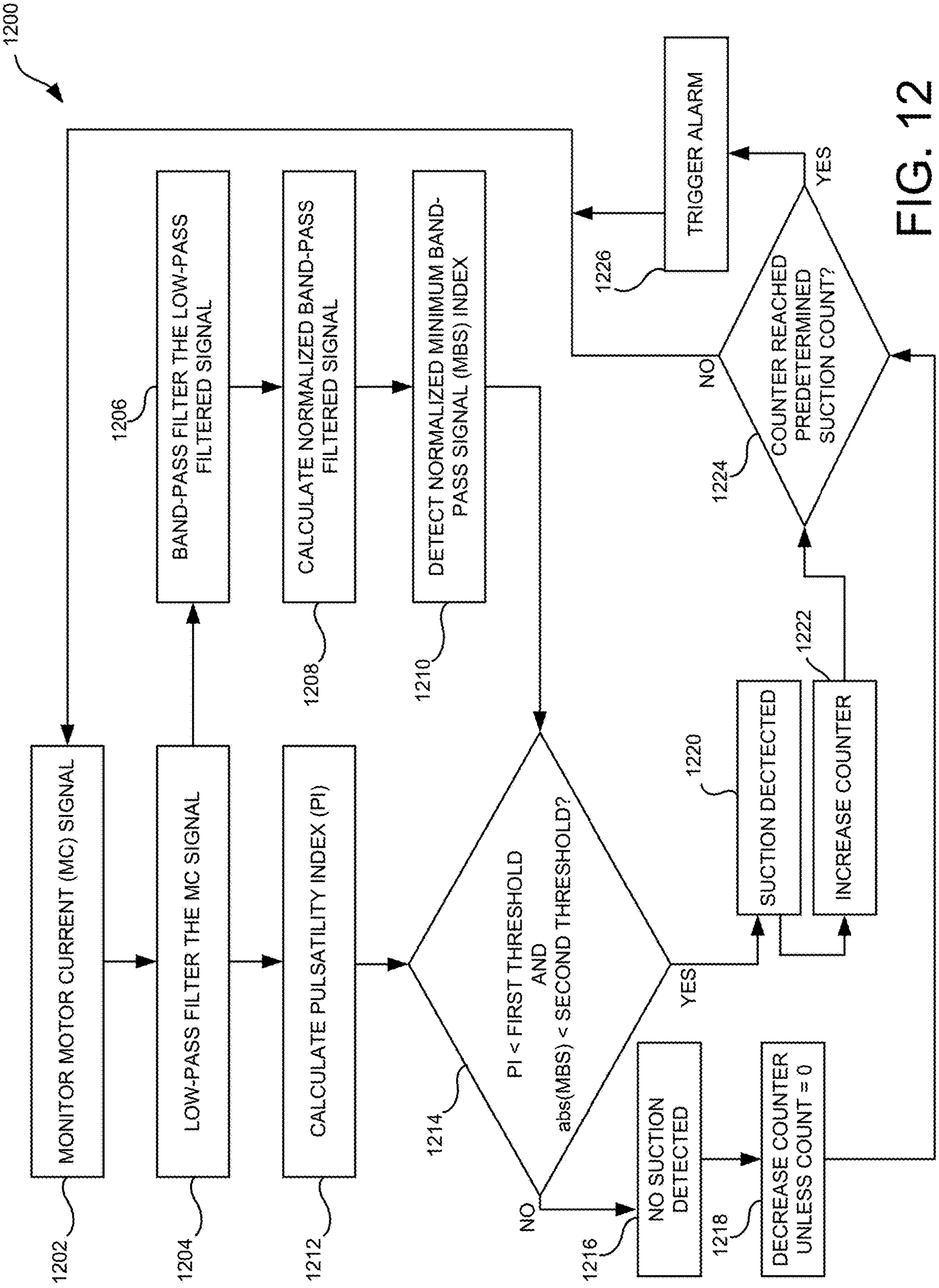
FIG. 12 is a flow chart of another method for detection suction events in accordance with the present technology.

Referring to FIG. 12, a method 1200 for detecting a suction event using the PI of the motor current and the MBS index during usage of a pump in a patient, such as pump 100, is shown in accordance with the present technology. It is to be appreciated that method 1200 may be performed or executed by one or more processors of the pump, such as processor 204 of pump 100, using the motor current of the pump as the only input.

Referring to FIG. 12, a method 1200 for detecting a suction event using both the PI of the motor current and MBS index value described above during usage of a pump in a patient, such as pump 100, is shown in accordance with the present technology. It is to be appreciated that method 1200 may be performed or executed by one or more processors of the pump system, such as processor 204 of pump 100, using the motor current of the pump as the only input.

Initially, in step 1202, the processor 204 monitors the motor current of the pump motor after deployment of the pump into the patient and activation of the pump. In step 1204, the motor current signal is filtered using a low-pass filter. For example, in one aspect, a 15 Hz low-pass filter, such as the second-order Butterworth Filter described above, may be used to filter the motor current signal. In step 1206, the low-pass filtered signal is band-pass filtered by processor 204 using a band-pass filter that passes frequencies of the signal in a predetermined range, such as, 0.5 to 5 Hz, as described above. For example, in one aspect, a sixth-order elliptic filter that passes frequencies ranging from 0.5 Hz to 5 Hz may be used to filter the low-pass filtered signal, as described above.

It is to be appreciated that the filtering in method 1200 may be implemented digitally by processor 204. Alternatively, processor 204 may control analogue filter circuits (including suitable low-pass and a band-pass filters), for example, included in control unit 200 or external to control unit 200, to low-pass filter and band-pass filter the motor current signal.

In step 1208, processor 204 calculates the normalized band-pass filtered signal of the band-pass signal by dividing each sample of the band-pass filtered signal of step 1206 by each corresponding sample of the low-pass filtered signal of step 1204 in accordance with Equation 3 above. In step 1210, processor 204 determines abs(MBS) by calculating the MBS index of the normalized band-pass filtered signal by detecting the minimum value within a predetermined time window (e.g., two seconds) of the normalized band-pass filtered motor current signal and determining the absolute value of the detected minimum value within the predetermined time window. In step 1212, processor 204 calculates the PI of the motor current of the low-pass filtered signal of step 1204 in accordance with Equation 2 above and in the manner described in relation to steps 606-610 above.

In step 1214, processor 204 compares the calculated PI of the motor current of step 1212 to a first predetermined threshold (e.g., approximately 0.15, as described above) and processor 204 compares abs(MBS) determined in step 1210 to a second predetermined threshold (e.g., approximately 0.07, as described above). In step 1214, a suction event is detected at 1220 if both PI and abs(MBS) are below their respective first and second thresholds. If, in step 1214, processor 204 determines that at least one of the calculated PI of the motor current is above the first predetermined threshold and/or the absolute value of the calculated MBS index is above the second threshold, the processor 204 determines that no suction is detected in step 1216.

Although method 1200 requires both the PI to be less than the first threshold and the abs(MBS) to be less than the second threshold in step 1214 in order to detect a suction event at step 1220, it should be understood that other approaches may be suitable depending on a desired specificity or sensitivity. In particular, the depicted method may promote specificity by requiring both threshold conditions to be satisfied before detecting a suction event at step 1220. In other aspects, such as if increased sensitivity preferred, suction may be detected if PI is less than the first threshold or abs(MBS) is less than the second threshold (i.e., suction is detected as long as one threshold condition is satisfied).

As described above, a counter may be implemented by processor 204 to balance the reliability and stability of the suction detection. The counter may be a stepwise counter or any other suitable counter, as described above.

For example, returning to method 1200 in FIG. 12, when no suction is detected based on the comparison at step 1214, processor 204 decreases or decrements the counter by 1 in step 1218. Alternatively, when suction is detected based on the comparison at step 2114, processor 204 increases or increments the counter by 1 in step 1222. As described above, if the counter is at 0, processor 204 will not decrease the counter to below 0, i.e., 0 is the floor of the counter. In step 1224, processor 204 determines if the counter has reached a predetermined suction count. If, in step 1224, processor 204 determines that the counter has not reached the predetermined suction count, processor 204 returns to monitoring the MC signal in step 1202 and method 1200 is executed again. Alternatively, if, in step 1224, processor 204 determines that the counter has reached the predetermined suction count, processor 204 triggers an alarm condition in step 1226 to alert the user of the pump 100 that a suction event has been detected and processor 204 resets the counter to 0. The alarm condition may comprise triggering one or more indicators for alerting a user of the detected alarm condition as described above in relation to step 624 of method 600. After triggering the alarm condition and resetting the counter to 0 in step 1226, the processor 204 then returns to monitoring the MC signal in step 1202 of method 1200.

In one aspect of method 1200, steps 1216 and 1220 may be removed and, in this aspect, processor 204 may determine that a suction event has occurred only if the predetermined suction count at step 1224 has been reached.

In another aspect of method 1200, steps 1218, 1222, and 1224 (the steps relating to the counter) may be removed from the method 1200 and, in this aspect, processor 204 triggers the alarm condition if a suction event is detected in step 1220 (based on the comparison at step 1214) and returns to monitoring the motor current in step 1202. If processor 204 does not detect a suction condition in step 1216, the method returns to monitoring the motor current in step 1202.

Selection of PI and MBS Thresholds.

There is often a trade-off between sensitivity and specificity in the methods described herein. In this regard, increasing the sensitivity of a method can decrease its specificity. With respect to method 1200 described above, this trade-off depends on the selection of the first and second thresholds used for comparison with the calculated PI and the MBS index, respectively. When the first threshold is approximately 0.15 and the second threshold is approximately 0.07, depending on the testing conditions, method 1200 has approximately 100% specificity (+/−5%) and approximately 70-90% sensitivity (+/−5%). Testing and Validation.

Suction detection method 1200 was tested and validated by inducing different suction conditions and cardiac or pulse pressure conditions and testing the performance of the suction detection. For example, suction detection was tested at baseline and altered cardiac states (using pharmaceutical interventions) and under induced suction events that were simulated using mechanical interventions. For example, this is summarized in Table 1 below:

TABLE 1

| Pharmacological and Mechanical Interventions | | | |
|---|---|---|---|
| Condition | Procedure | | |
| Suction | IVC occlusion | pump into apex | inlet on valve |
| Pulse Pressure | Phenylephrine | Beta-Blocker | microbead injection |

As shown in the table above, three types of suction were induced during testing: IVC occlusion (using a circulation occlusion tool (e.g., an inflatable balloon) to block the flow into the ventricle to simulate IVC occlusion in a patient), placement of the pump into the apex, and placement of the inlet of the pump into on a valve. Moreover, various cardiac or pulse pressure conditions were induced by introduction of beta blockers (to induce low pressure), phenylephrine (to induce high pressure), and microbead injection (to induce cardiogenic shock (CGS)).

Figure 13:
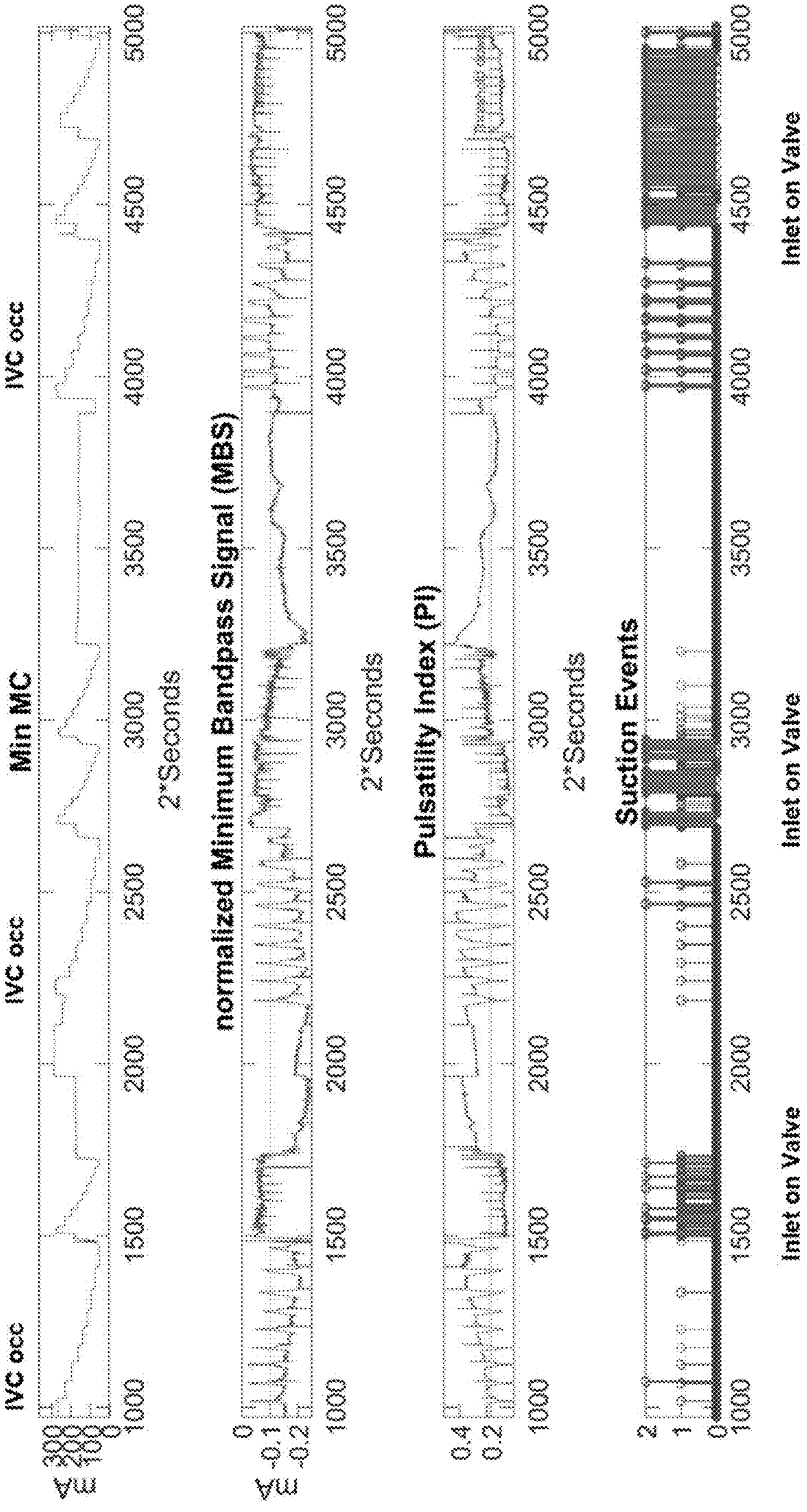
FIGS. 13-15 illustrate results of testing a suction detection method in accordance with the present technology.

An example of testing performed when the speed of the pump was ramped and under different suction conditions induced during animal study is shown in FIG. 13 in accordance with the present technology. As shown, the PI of the motor current signal and the normalized band-pass signal were obtained in accordance with Equations 2 and 3 above and successfully used to detect suction events (IVC occlusion and inlet on valve) within 2 second windows of the signal.

Table 2 below shows different pressure conditions used during the testing performed.

TABLE 2

| Pressure Conditions During Loop Testing | | |
|---|---|---|
| Condition | Aortic Pressure* (mmHg) | Ventricular Pressure* (mmHg) |
| Hypertensive | 140/90 | 140/0 |
| Low Normal | 90/50 | 90/0 |
| Cardiogenic Shock | 60/40 | 60/0 |
| Partial Decoupled | 70/60 | 50/0 |

Results.

Below, Table 3 includes a summary of results of various testing of the suction detection methods performed with different pumps, during animal studies or under simulated environments, with and without different types of induced suction, and under different induced pressure conditions.

TABLE 3

| Validation Results | | | | | | | | | | | | |
|---|---|---|---|---|---|---|---|---|---|---|---|---|
| Pressure | Suction/Type | Animal | Pump Serial No. | P1 | P2 | P3 | P4 | P5 | P6 | P7 | P8 | P9 |
| CGS | IVC | Yes | 314006 | TP | FN | FN | FN | TP | TP | FN | TP | TP |
| CGS | inlet on valve | Yes | 314006 | TP | TP | TP | TP | TP | TP | TP | TP | TP |
| CGS | pump into apex | Yes | 314006 | TP | TP | TP | TP | TP | TP | TP | TP | TP |
| CGS | No | Yes | 314006 | TN | TN | TN | TN | TN | TN | TN | TN | TN |
| High | IVC | Yes | 314006 | FN | FN | FN | FN | FN | FN | FN | FN | TP |
| High | inlet on valve | Yes | 314006 | FN | FN | FN | TP | TP | TP | TP | TP | TP |
| High | pump into apex | Yes | 314006 | TP | TP | TP | TP | TP | TP | TP | TP | TP |
| High | No | Yes | 314006 | TN | TN | TN | TN | TN | TN | TN | TN | TN |
| Normal | IVC | Yes | 314006 | TP | FN | FN | FN | FN | FN | TP | TP | TP |
| Normal | No | Yes | 314006 | TN | TN | TN | TN | TN | TN | TN | TN | TN |
| Normal | inlet on valve | Yes | 314006 | TP | TP | TP | TP | TP | FN | TP | TP | TP |
| High | IVC | Yes | 4726 | FN | FN | FN | FN | FN | FN | FN | TP | TP |
| High | inlet on valve | Yes | 4726 | FN | FN | FN | FN | TP | TP | TP | TP | TP |
| High | pump into apex | Yes | 4726 | FN | FN | FN | FN | TP | TP | TP | TP | TP |
| High | No | Yes | 4726 | TN | TN | TN | TN | TN | TN | TN | TN | TN |
| LOW | IVC | Yes | 4726 | TP | FN | TP | TP | TP | TP | TP | TP | TP |

TABLE 3-continued

| Validation Results | | | | | | | | | | | | |
|---|---|---|---|---|---|---|---|---|---|---|---|---|
| Pressure | Suction/Type | Animal | Pump Serial No. | P1 | P2 | P3 | P4 | P5 | P6 | P7 | P8 | P9 |
| LOW | inlet on valve | Yes | 4726 | FN | TP | TP | TP | TP | TP | TP | TP | TP |
| LOW | pump into apex | Yes | 4726 | TP | TP | TP | TP | TP | TP | TP | TP | TP |
| Low | No | Yes | 4726 | TN | TN | TN | TN | TN | TN | TN | TN | TN |
| Normal | IVC | Yes | 4726 | FN | FN | FN | FN | TP | FN | TP | TP | TP |
| Normal | pump into apex | Yes | 4726 | TP | TP | TP | TP | FN | FN | TP | TP | TP |
| Normal | No | Yes | 4726 | TN | TN | TN | TN | TN | TN | TN | TN | TN |
| Normal | inlet on valve | Yes | 4726 | TP | TP | TP | TP | TP | TP | TP | TP | TP |
| High | inflow occlusion | NO | 475 | N/A | TP | TP | TP | TP | TP | TP | TP | TP |
| High | NO | NO | 475 | N/A | TN | TN | TN | TN | TN | TN | TN | TN |
| Low | inflow occlusion | NO | 475 | N/A | TP | TP | TP | TP | TP | TP | TP | TP |
| Low | NO | NO | 475 | N/A | TN | TN | TN | TN | TN | TN | TN | TN |
| Normal | inflow occlusion | NO | 475 | N/A | TP | TP | TP | TP | TP | TP | TP | TP |
| Normal | NO | NO | 475 | N/A | TN | TN | TN | TN | TN | TN | TN | TN |
| High | inflow occlusion | NO | 466 | N/A | TP | TP | TP | TP | TP | TN | TP | TP |
| High | NO | NO | 466 | N/A | TN | TN | TN | TN | TN | TN | TN | TN |
| Low | inflow occlusion | NO | 466 | N/A | TP | TP | TP | TP | TP | TP | TP | TP |
| Low | NO | NO | 466 | N/A | TN | TN | TN | TN | TN | TN | TN | TN |
| Normal | inflow occlusion | NO | 466 | N/A | TP | TP | TP | TP | TP | TP | TP | TP |
| Normal | NO | NO | 466 | N/A | TN | TN | TN | TN | TN | TN | FP | FP |
| High | inflow occlusion | NO | 463 | N/A | TP | TP | TP | TP | TP | FN | TP | TP |
| High | NO | NO | 463 | N/A | TN | TN | TN | TN | TN | TN | TN | TN |
| Low | inflow occlusion | NO | 463 | N/A | TP | TP | TP | TP | TP | TP | TP | TP |
| Low | NO | NO | 463 | N/A | TN | TN | TN | TN | TN | TN | TN | TN |
| Normal | inflow occlusion | NO | 463 | N/A | TP | TP | TP | TP | TP | TP | TP | TP |
| Normal | NO | NO | 463 | N/A | TN | TN | TN | TN | TN | TN | TN | TN |

It is to be appreciated that in the table above "TP" is a true positive result where suction was correctly detected, "TN" is a true negative result where absence of suction was correctly detected, "FP" is a false positive where suction was incorrectly detected, and "FN" is a false negative where absence of suction was incorrectly detected.

As shown in Table 3, only 2 false positive results were observed during the animal and simulated benchtop testing performed. Table 4 below shows the calculation of sensitivity and specificity achieved during testing of the suction detection of the present technology. As shown, a very high specificity of 98% and good sensitivity of 79% was achieved by the suction detection method using the PI and MBS index of the present technology in the testing summarized above.

TABLE 4

| Calculation of Specificity and Sensitivity | | |
|---|---|---|
| Overall Results | Suction Condition | No Suction Condition |
| Positive Suction | 177 | 2 |
| Negative Suction | 46 | 125 |
| | 0.79 | 0.98 |

It is to be appreciated that the duration of the suction event may affect the sensitivity and the suction detection. For example, referring to FIG. 14, the results of a further animal study performed is shown where the duration of each induced suction event (IVC occlusion) was increased (as long as it was tolerable by the animal) and the speed of the pump was ramped. During this animal testing, the suction detection using the PI and MBS index was able to detect suction in hypertensive conditions at various pump speeds. The specificity of the suction detection was approximately 100% (+/−5%) and the sensitivity of the suction detection was approximately 89% (+/−5%).

Referring to FIG. 15, the results of applying the suction detection method 1200 of the present technology to human study data is shown. As shown, the suction detection method 1200 retrospectively detected and confirmed suction events in the human study data surmised from the pulsatility index information.

Figure 14:
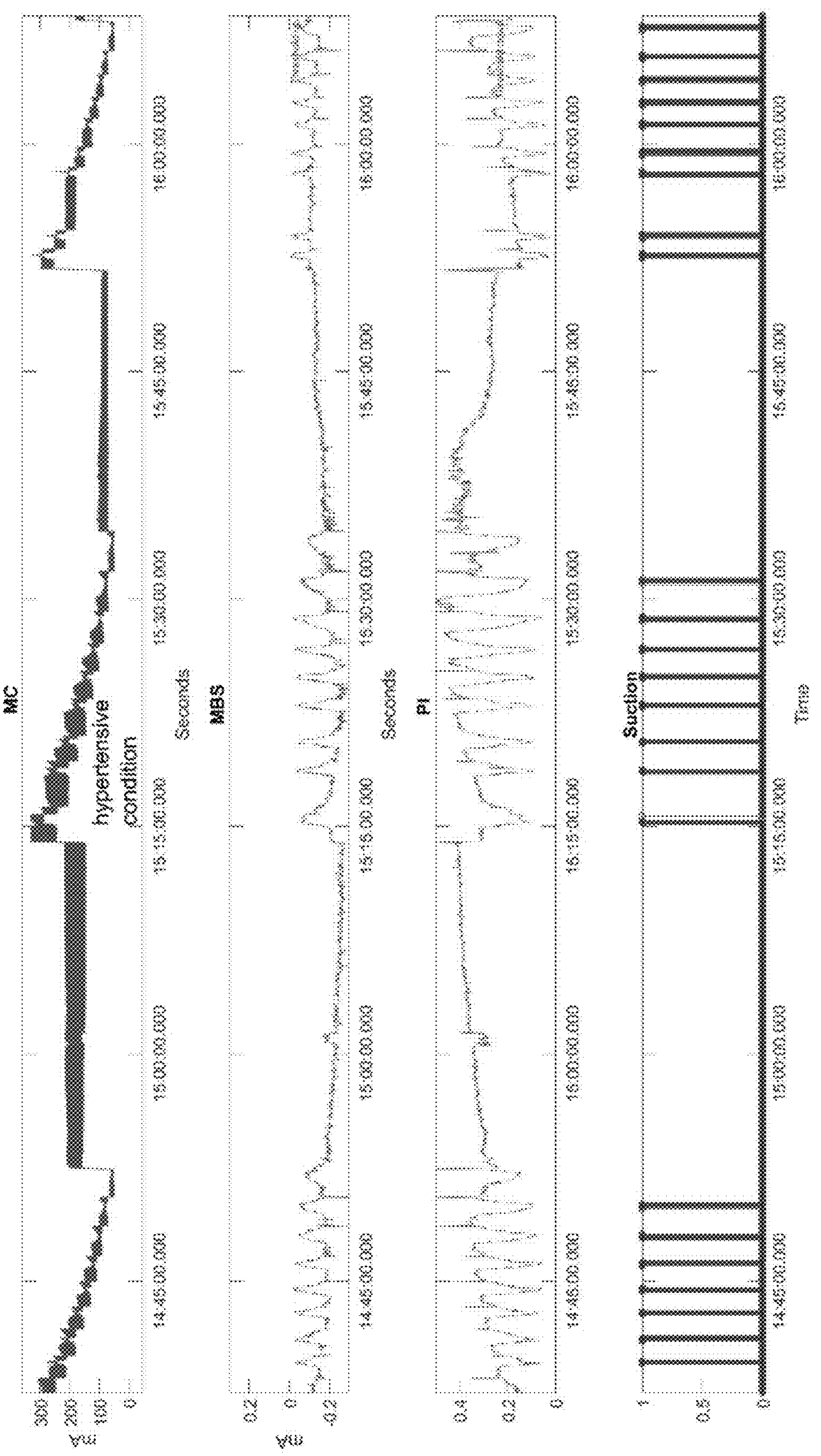

As shown in FIGS. 13-15, as noted previously, the current of the normalized minimum bandpass signal may be negative. Thus, to account for the negative current of the normalized minimum bandpass signal in the suction detection, as described above, the MBS index may be calculated by detecting the minimum value of the normalized minimum bandpass signal within the predetermined window of the signal and then the absolute value of the detected minimum value is determined (abs(MBS)) for comparison with the second predetermined threshold to detect suction events (when abs(MBS) is below threshold).

It is to be appreciated that in any of the methods described above, the parameters of the methods, e.g., predetermined time windows and thresholds used for detection of suction events may be adjustable by the user via user input to control unit 200 (e.g., user input to user interface 206). Moreover, the particular suction detection method to be used (e.g., method 600, 1100, 1200) may also be selectable by the user via user input to control unit 200.

It is to be appreciated that in any of the methods described above, responsive to a suction event being detected (or an alarm condition being triggered), processor 204 may output a notification message to the user (e.g., displayed via interface 206) or otherwise communicated to the user (e.g., via an indicator light or audible message, etc.) to lower the speed of the pump so that the suction event may be resolved. In one aspect, the alarm condition in the above-described methods comprises the message or other communication to the user to lower the pump speed. In one aspect, responsive to a suction event being detected (or an alarm condition being triggered), processor 204 may automatically control the motor current to lower the speed of the pump to a predetermined speed threshold to resolve the suction event.

In one aspect, a blood pump is provided comprising: an inlet, an outlet, a rotor, a motor for driving rotation of the rotor to convey blood from the inlet to the outlet, and at least one processor. The at least one processor is configured to: monitor a motor current signal of the motor, filter the motor current signal, calculate a pulsatility index of the motor current signal based on the filtered motor current signal, compare the calculated pulsatility index to a predetermined threshold, and detect an occurrence of a suction event based on the comparison.

In any of the aspects above, the motor current signal may be filtered using a low-pass filter.

In any of the aspects above, the low-pass filter may be a second-order Butterworth filter.

In any of the aspects above, the low-pass filter may pass frequencies from 0 Hz to 15 Hz.

In any of the aspects above, the at least one processor may be configured to calculate the pulsatility index of the motor current signal by: detecting a maximum motor current (max MC) and a minimum motor current (min MC) within a predetermined window of the filtered motor current signal, calculating a mean motor current (mean MC) within the predetermined window of the filtered motor current signal, and calculating the pulsatility index of the motor current signal according to the following equation 4:

$$\text{Pulsatility Index} = \frac{(\max MC) - (\min MC)}{\text{mean } MC} \quad \text{(Equation 4)}$$

In any of the aspects above, the predetermined window may be approximately 2 seconds.

In any of the aspects above, the predetermined threshold may be approximately 0.15.

In any of the aspects above, the occurrence of the suction event may be detected when the calculated pulsatility index is below the predetermined threshold.

In any of the aspects above, the at least one processor may be configured to maintain a suction counter including a suction count representing a number suction events detected.

In any of the aspects above, the at least one processor may be configured to trigger an alarm condition to alert a user that a suction event is occurring when the counter reaches a predetermined suction count.

In any of the aspects above, the predetermined suction count may be 4.

In any of the aspects above, the at least one processor may be configured to increase the counter by 1 when an occurrence of a suction event is detected and decrease the counter by 1 when the occurrence of a suction event is not detected.

In any of the aspects above, the at least one processor may be configured to detect the occurrence of the suction event without information relating to sensed blood pressure.

In any of the aspects above, the blood pump may be a heart pump insertable into a ventricle of a patient's heart.

In another aspect, a blood pump is provided comprising: an inlet, an outlet, a rotor, a motor for driving rotation of the rotor to convey blood from the inlet to the outlet, and at least one processor. The at least one processor is configured to: monitor a motor current signal of the motor, low-pass filter the motor current signal, band-pass filter the low-pass filtered motor current signal, normalize the band-pass filtered motor current signal, calculate an index value based on the normalized band-pass filtered motor current signal, compare the calculated index value to a predetermined threshold, and detect an occurrence of a suction event based on the comparison.

In any of the aspects above, the motor current signal may be low-pass filtered using a second-order Butterworth filter.

In any of the aspects above, the motor current signal may be low-pass filtered using a low-pass filter that passes frequencies from 0 Hz to 15 Hz.

In any of the aspects above, the low-pass filtered motor current signal may be band-pass filtered using a sixth-order elliptic filter.

In any of the aspects above, the low-pass filtered motor current signal may be band-pass filtered using a band-pass filter that passes frequencies from 0.5 Hz to 5 Hz.

In any of the aspects above, the at least one processor may be configured to calculate the index value by detecting a minimum value within a predetermined window of the normalized band-pass filtered motor current signal and calculating the absolute value of the detected minimum value within the predetermined window.

In any of the aspects above, the predetermined window may be approximately 2 seconds.

In any of the aspects above, the at least one processor may calculate the normalized band-pass filtered motor current signal by dividing each sample in the band-pass filtered motor current signal by each corresponding sample in the low-pass filtered motor current signal.

In any of the aspects above, the predetermined threshold may be approximately 0.07.

In any of the aspects above, the occurrence of the suction event may be detected when the calculated index value is below the predetermined threshold.

In any of the aspects above, the at least one processor may be configured to maintain a suction counter including a suction count representing a number suction events detected.

In any of the aspects above, the at least one processor may be configured to trigger an alarm condition to alert a user that a suction event is occurring when the counter reaches a predetermined suction count.

In any of the aspects above, the predetermined suction count may be 4.

In any of the aspects above, the at least one processor may be configured to increase the counter by 1 when an occurrence of a suction event is detected and decrease the counter by 1 when the occurrence of a suction event is not detected.

In any of the aspects above, the at least one processor may be configured to detect the occurrence of the suction event without information relating to sensed blood pressure.

In any of the aspects above, the blood pump may be a heart pump insertable into a ventricle of a patient's heart.

In another aspect, a blood pump is provided comprising: an inlet, an outlet, a rotor, a motor for driving rotation of the rotor to convey blood from the inlet to the outlet, and at least one processor configured to: monitor a motor current signal of the motor, low-pass filter the motor current signal, calculate a pulsatility index of the motor current signal based on the low-pass filtered motor current signal, band-pass filter the low-pass filtered motor current signal, normalize the band-pass filtered motor current signal, calculate an index value based on the normalized band-pass filtered signal, compare the calculated pulsatility index to a first predetermined threshold and the calculated index value to a second predetermined threshold, and detect an occurrence of a suction event based on the comparison of the calculated pulsatility index to the first predetermined threshold and the calculated index value to the second predetermined threshold.

From the foregoing and with reference to the various figure drawings, those skilled in the art will appreciate that certain modifications can also be made to the present disclosure without departing from the scope of the same. While several aspects of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular aspects. Those skilled in the art will envision other modifications within the scope and spirit of the claims appended hereto.

The invention claimed is:

1. A blood pump comprising:

an inlet and an outlet;

a rotor;

a motor for driving rotation of the rotor to convey blood from the inlet to the outlet; and at least one processor configured to:

monitor a motor current signal of the motor, filter the motor current signal, calculate a pulsatility index of the motor current signal based on the filtered motor current signal, compare the calculated pulsatility index to a predetermined threshold, detect an occurrence of a suction event based on the comparison, and maintain a suction counter including a suction count representing a number of suction events detected.

2. The blood pump of claim 1, wherein the motor current signal is filtered using a low-pass filter.

3. The blood pump of claim 2, wherein the low-pass filter is a second-order Butterworth filter.

4. The blood pump of claim 2, wherein the low-pass filter passes frequencies from 0 Hz to 15 Hz.

5. The blood pump of claim 1, wherein the at least one processor is configured to calculate the pulsatility index of the motor current signal by:

detecting a maximum motor current (max MC) and a minimum motor current (min MC) within a predetermined window of the filtered motor current signal, calculating a mean motor current (mean MC) within the predetermined window of the filtered motor current signal, and calculating the pulsatility index of the motor current signal according to the following equation:

$$\text{Pulsatility Index} = \frac{(\max MC) - (\min MC)}{\text{mean } MC}.$$

6. The blood pump of claim 5, wherein the predetermined window is approximately 2 seconds.

7. The blood pump of claim 1, wherein the predetermined threshold is approximately 0.15.

8. The blood pump of claim 7, wherein the occurrence of the suction event is detected when the calculated pulsatility index is below the predetermined threshold.

9. The blood pump of claim 1, wherein the at least one processor is configured to trigger an alarm condition to alert a user that a suction event is occurring when the counter reaches a predetermined suction count.

10. The blood pump of claim 9, wherein the predetermined suction count is 4.

11. The blood pump of claim 1, wherein the at least one processor is configured to increase the counter by 1 when an occurrence of a suction event is detected and decrease the counter by 1 when the occurrence of a suction event is not detected.

12. The blood pump of claim 1, wherein the at least one processor is configured to detect the occurrence of the suction event without information relating to sensed blood pressure.

13. The blood pump of claim 1, wherein the blood pump is a heart pump insertable into a ventricle of a patient's heart.

14. A blood pump comprising:

an inlet and an outlet;

a rotor;

a motor for driving rotation of the rotor to convey blood from the inlet to the outlet; and at least one processor configured to:

monitor a motor current signal of the motor, low-pass filter the motor current signal, band-pass filter the low-pass filtered motor current signal, normalize the band-pass filtered motor current signal, calculate an index value based on the normalized band-pass filtered motor current signal, compare the calculated index value to a predetermined threshold, detect an occurrence of a suction event based on the comparison, and maintain a suction counter including a suction count representing a number of suction events detected.

15. The blood pump of claim 14, wherein the motor current signal is low-pass filtered using one of a second-order Butterworth filter or a low-pass filter that passes frequencies from 0 Hz to 15 Hz, or is band-pass filtered using one of a sixth-order elliptic filter or using a band-pass filter that passes frequencies from 0.5 Hz to 5 Hz.

16. The blood pump of claim 14, wherein the at least one processor is configured to calculate the index value by detecting a minimum value within a predetermined window of the normalized band-pass filtered motor current signal and determining an absolute value of the detected minimum value within the predetermined window.

17. The blood pump of claim 16, wherein the predetermined window is approximately 2 seconds.

18. The blood pump of claim 14, wherein the at least one processor calculates the normalized band-pass filtered motor current signal by dividing each sample in the band-pass filtered motor current signal by each corresponding sample in the low-pass filtered motor current signal.

19. The blood pump of claim 14, wherein the predetermined threshold is approximately 0.07.

20. The blood pump of claim 14, wherein the occurrence of the suction event is detected when the calculated index value is below the predetermined threshold.

21. The blood pump of claim 14, wherein the at least one processor is configured to trigger an alarm condition to alert a user that a suction event is occurring when the suction counter reaches a predetermined suction count.

22. The blood pump of claim 21, wherein the predetermined suction count is 4.

23. The blood pump of claim 21, wherein the at least one processor is configured to increase the suction counter by 1 when an occurrence of a suction event is detected and decrease the suction counter by 1 when the occurrence of a suction event is not detected.

24. The blood pump of claim 14, wherein the at least one processor is configured to detect the occurrence of the suction event without information relating to sensed blood pressure.

25. The blood pump of claim 14, wherein the blood pump is a heart pump insertable into a ventricle of a patient's heart.

26. A blood pump comprising:

an inlet and an outlet;

a rotor;

a motor for driving rotation of the rotor to convey blood from the inlet to the outlet; and at least one processor configured to:

monitor a motor current signal of the motor, low-pass filter the motor current signal, calculate a pulsatility index of the motor current signal based on the low-pass filtered motor current signal, band-pass filter the low-pass filtered motor current signal, normalize the band-pass filtered motor current signal, calculate an index value based on the normalized band-pass filtered motor current signal, compare the calculated pulsatility index to a first predetermined threshold and the calculated index value to a second predetermined threshold, detect an occurrence of a suction event based on the comparison of the calculated pulsatility index to the first predetermined threshold and the calculated index value to the second predetermined threshold, and maintain a suction counter including a suction count representing a number of suction events detected.

* * * * *